US008381594B2

(12) United States Patent
Adachi et al.

(10) Patent No.: US 8,381,594 B2
(45) Date of Patent: Feb. 26, 2013

(54) ACOUSTIC TRANSDUCER AND IMAGE GENERATION APPARATUS

(75) Inventors: Hideo Adachi, Iruma (JP); Tomoo Kamakura, Kawasaki (JP)

(73) Assignee: Olympus Medical Systems Corp., Tokyo (JP)

(*) Notice: Subject to any disclaimer, the term of this patent is extended or adjusted under 35 U.S.C. 154(b) by 290 days.

(21) Appl. No.: 12/758,249

(22) Filed: Apr. 12, 2010

(65) Prior Publication Data

US 2010/0251823 A1    Oct. 7, 2010

Related U.S. Application Data

(63) Continuation of application No. PCT/JP2009/068528, filed on Oct. 28, 2009.

(30) Foreign Application Priority Data

Nov. 4, 2008 (JP) ................................. 2008-283462

(51) Int. Cl.
*G01N 29/24* (2006.01)
*G01N 29/34* (2006.01)
(52) U.S. Cl. ................. 73/632; 73/627; 73/642; 367/92
(58) Field of Classification Search .................. 73/627; 367/92, 94, 103, 87; 600/437
See application file for complete search history.

(56) References Cited

U.S. PATENT DOCUMENTS

| | | | |
|---|---|---|---|
| 5,903,516 A * | 5/1999 | Greenleaf et al. | 367/92 |
| 7,196,970 B2 * | 3/2007 | Moon et al. | 367/92 |
| 2005/0075565 A1 | 4/2005 | Satoh | |
| 2006/0169029 A1 * | 8/2006 | Heyman | 73/52 |
| 2008/0013405 A1 | 1/2008 | Moon et al. | |

FOREIGN PATENT DOCUMENTS

| | | |
|---|---|---|
| JP | Sho 55-40371 | 3/1980 |
| JP | 58-178253 | 10/1983 |
| JP | 08-080300 | 3/1996 |
| JP | 2003-116848 | 4/2003 |
| JP | 2003-265466 | 9/2003 |
| JP | 2005-087576 | 4/2005 |
| JP | 2006-025109 | 1/2006 |
| JP | 2007-281164 | 10/2007 |
| JP | 2008-020429 | 1/2008 |
| JP | 2008-022347 | 1/2008 |

OTHER PUBLICATIONS

Kamakura, T. et al., "Parametric audible sounds by phase-cancellation excitation of primary waves", Journal of the Acoustical Society of America (2008), 123(5):3694.

* cited by examiner

*Primary Examiner* — Peter Macchiarolo
*Assistant Examiner* — Rose M Miller
(74) *Attorney, Agent, or Firm* — Scully, Scott, Murphy & Presser, P.C.

(57) ABSTRACT

An acoustic transducer has a first transducer which transmits an acoustic primary wave having two frequency components, and a second transducer which, in order to receive a reflected wave of an acoustic secondary wave generated with propagation of the acoustic primary wave, is disposed so that a region for receiving the reflected wave is superimposed on the first transducer as seen along the direction of transmission of the acoustic primary wave.

24 Claims, 21 Drawing Sheets

ACOUSTIC TRANSDUCER AND IMAGE GENERATION APPARATUS

CROSS REFERENCE TO RELATED APPLICATION

This application is a continuation application of PCT/JP2009/068528 filed on Oct. 28, 2009 and claims benefit of Japanese Application No. 2008-283462 filed in Japan on Nov. 4, 2008, the entire contents of which are incorporated herein by this reference.

BACKGROUND OF THE INVENTION

1. Field of the Invention

The present invention relates to an acoustic transducer and to an image generation apparatus. More particularly, the present invention relates to an acoustic transducer which transmits an acoustic primary wave and receives an acoustic secondary wave and to an image generation apparatus using a plurality of the acoustic transducers.

2. Description of the Related Art

It has been known that when an acoustic wave of a large amplitude is radiated, a waveform distortion (a change in waveform) occurs due to the nonlinearity of a propagation medium such that the waveform of the propagated wave differs from the radiated original waveform (initial waveform).

The phenomenon of the occurrence of this distortion appears particularly frequently in an ultrasound region exceeding audible frequencies. Moreover, it is known that waveform distortion does not occur abruptly at a certain distance from the acoustic transducer but appears in a wide ultrasound frequency range based on a distortion accumulation effect such that the amount of distortion increases gradually with propagation. The radiated acoustic wave of the initial waveform is hereinafter referred to as "acoustic primary wave". Also, a nonlinear acoustic wave generated based on the above-described distortion accumulation effect is referred to as "acoustic secondary wave".

When an acoustic primary wave is formed of a single frequency component, acoustic secondary waves having integer-multiple frequency components are generated. These waves are called a second harmonic signal, a third harmonic signal, an nth harmonic signal and so on. Medical ultrasound imaging apparatuses using these waves are on the market.

On the other hand, when an acoustic primary wave is formed of two frequency components, a sum signal and a difference signal are generated at two frequencies as nonlinear acoustic waves. The latter is ordinarily called a parametric signal. In some case, each of these signals is called a parametric signal. The parametric signal is an acoustic secondary wave of a frequency $|f1-f2|$ or $|f1+f2|$ generated by a nonlinear effect of an acoustic primary wave having a frequency of $f1$ and an acoustic primary wave having a frequency of $f2$ as the acoustic primary waves propagate. The parametric signal has such a characteristic that its amplitude increases by the accumulation effect with propagation. Description will be made by assuming that parametric signals referred to below are difference signals unless otherwise noted.

The parametric signal has such a characteristic as to be capable of setting a long propagation distance (i.e., a large penetration depth) because its frequency is lower than that of the acoustic primary wave. Further, the parametric signal is known to have, as its other characteristics, in comparison with a fundamental wave of the same frequency, a reduced amount of expansion of the beam (i.e., high lateral resolution) and freedom from forming a sidelobe (i.e., having high contrast resolution).

On the other hand, the parametric signal also has a characteristic of being inferior in resolution in the depth direction than the acoustic primary wave (fundamental wave) because its frequency is lower than that of the acoustic primary wave. Further, in parametric imaging using the parametric signal, it is preferable to suppress the acoustic primary wave component which mixes with the parametric signal and harmonics of the parametric signal to lowest possible levels. The measures taken to do so enable high S/N ratio imaging. This condition is the same as the necessity of a pulse inversion technique in harmonic imaging already put to practical use.

In the pulse inversion technique, a voltage signal in a normal phase having a component of a frequency f is first applied to transmit an acoustic primary wave in the normal phase and, after a time interval from this transmission, a voltage signal in the opposite phase having a component of the frequency f is applied to transmit an acoustic primary wave in the opposite phase. The fundamental wave components of these two acoustic waves are wholly identical in waveform to each other, though phase-inverted relative to each other. Thus, ultrasounds in phase opposition to each other are transmitted at different times.

However, harmonics, e.g., the second harmonics are squared to form positive acoustic secondary waves irrespective of whether the polarity of the applied voltage is positive or negative. When two groups of acoustic primary wave components and acoustic secondary wave components such as described above are added together, only acoustic secondary waves, which are harmonic components, remain, while the acoustic primary components become zero when added together because they are in phase opposition to each other.

As a method of adding together two acoustic waves, a method is known in which a signal obtained by converting a preceding received acoustic wave into voltages is temporarily stored in a memory and is read out when a signal obtained by converting a following received acoustic wave into voltages is received, and addition processing is performed on the signals to extract only harmonic components.

It is well known that remaining of the fundamental wave component relates or contributes to the generation of a sidelobe and can be a cause of a speckle. Also, the amount of speckle is increased with increase in the amount of the fundamental component remaining.

As described above, the conventional pulse inversion technique is a method to suppress a fundamental wave component by canceling out acoustic primary waves inverted on the time axis. As a proposition relating to the method to suppress in this way an acoustic primary wave which is a fundamental wave component, a proposition has been made in the field of audible sound parametric speaker techniques to solve a problem that an audible sound reproduced by a parametric speaker contains large amounts of harmonic distortion and intermodulation distortion, is inferior in sound clarity to a corresponding sound reproduced by an electrodynamic speaker and, in some case, causes a listener to have a feeling of discomfort. A technique according to this proposition is disclosed, for example, in a document: Tomoo Kamakura, Shinichi Sakai, Hideyuki Nomura, Masahiko Akiyama "Parametric audible sounds by phase-cancellation excitation of primary waves.", J. Acoust. Soc. Am. Volume 123, Issue 5, pp. 3694-3694 (May 2008).

This proposition is a method which enables suppression of acoustic primary waves and generation of acoustic secondary waves in an audible sound region by transmitting acoustic primary waves in phase opposition to each other and by utilizing a sound field region where acoustic primary waves can be suppressed.

Propositions about a case of ultrasound in which a parametric acoustic wave is propagated in a living tissue or water have also been made.

For example, an ultrasound image processing method using a parametric acoustic transducer method has been proposed in which an amplitude-modulated wave produced by amplitude modulation on a center frequency through a certain frequency width or an ultrasound having two frequency components is transmitted from an ultrasound probe to a subject; an echo generated in the subject and containing at least a differential frequency component is received by the ultrasound probe; and the received echo is signal processed to obtain an ultrasound image. A technique according to this proposition is disclosed, for example, in Japanese Patent Application Laid-Open Publication No. 8-80300. According to this proposition, diagnosis by means of an ultrasound image with a small attenuation is enabled.

A method has also been proposed in which an ultrasound having a first frequency component and an ultrasound having a second frequency component are transmitted from a first ultrasound transducer and a second ultrasound transducer, respectively, at a desired angle from each other so as to intersect each other at a target diseased part, and a difference signal, a sum signal, a harmonic signal and a frequency-divided signal contained in a reflection signal from the diseased part position at which the waves intersect each other are received by the first ultrasound transducer. A technique according to this proposition is disclosed, for example, in Japanese Patent Application Laid-Open Publication No. 2003-116848. The parametric diagnostic apparatus according to this proposition is capable of clearly displaying the shape of a diseased part or the like.

In each of the techniques according to the above-described propositions, the characteristics of a parametric signal, i.e., a small attenuation, capability of propagating an acoustic wave signal through a large distance, and a phenomenon in which the directionality is higher than that of a fundamental wave of the same frequency, are utilized.

SUMMARY OF THE INVENTION

An acoustic transducer of the present invention has a first transducer which transmits an acoustic primary wave having two frequency components, and a second transducer which, in order to receive a reflected wave of an acoustic secondary wave generated with propagation of the acoustic primary wave, is disposed so that a region for receiving the reflected wave is superimposed on the first transducer as seen along the direction of transmission of the acoustic primary wave.

DETAILED DESCRIPTION OF THE PREFERRED EMBODIMENT(S)

Embodiments of the present invention will be described with reference to the drawings.

First Embodiment

A first embodiment of the present invention will be described. A transmitting portion which transmits an acoustic primary wave having two frequency components will first be described.

Figure 1:
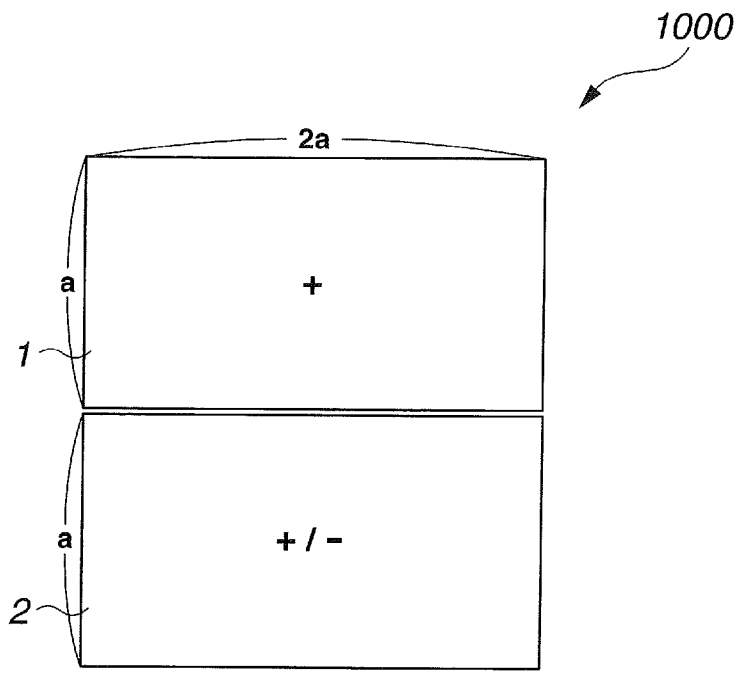
FIG. 1 is a plan view of a transmitting portion of an acoustic transducer according to a first embodiment of the present invention.
Figure 2:
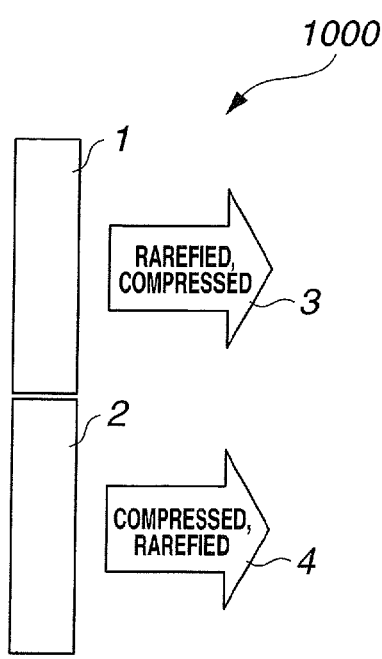
FIG. 2 is a side view for explaining the state of a side surface of the transmitting portion of the acoustic transducer and the state of acoustic waves according to the first embodiment of the present invention.

FIGS. 1 and 2 are diagrams for explaining the basic structure of a transmitting portion of an acoustic transducer according to the present embodiment. FIG. 1 is a plan view of the transmitting portion of the acoustic transducer according to the present embodiment. FIG. 2 is a side view for explaining the state of a side surface of the transmitting portion of the acoustic transducer and the state of acoustic waves according to the present embodiment.

As shown in FIG. 1, a transmitting portion 1000, which is a transducer, has regions for transmitting including a pair of acoustic transducers (also referred to as "transducer" below) 1 and 2 disposed adjacent to each other. The two transducers 1 and 2 constitute the transmitting portion 1000 of the parametric acoustic transducer. In the present embodiment, each of the transducers 1 and 2 is a diaphragm of a piezoelectric element in the form of a thin plate having a rectangular shape. In the rectangular shape, the length of one side is a and the length of another side is 2a. An acoustic wave transmitted from one of the pair of transducers and an acoustic wave transmitted from the other transducer are phase-inverted relative to each other, as described below. That is, the transmitting portion 1000 has such a configuration as to be capable of transmitting from the two regions acoustic waves phase-inverted relative to each other.

As shown in FIG. 2, the two transducers 1 and 2 are driven so that if an acoustic primary wave 3 outputted from the transducer 1 is rarefied, compressed, rarefied, . . . , an acoustic primary wave 4 outputted from the transducer 2 is compressed, rarefied, compressed . . . .

Figure 3:
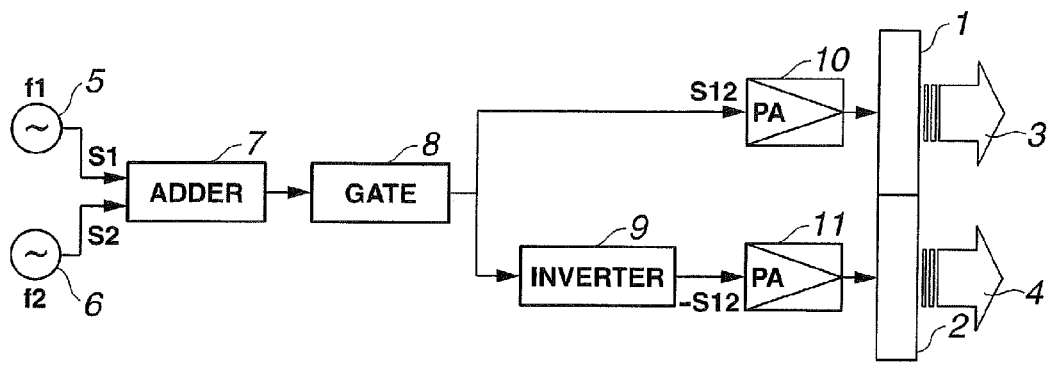
FIG. 3 is a diagram of a transmitting circuit for driving the transmitting portion according to the first embodiment of the present invention.

FIG. 3 is a diagram of a transmitting circuit for driving the transmitting portion 1000 according to the present embodiment.

As shown in FIG. 3, the transmitting circuit is configured by including two signal sources 5 and 6, an adder 7, a gate 8, an inverter 9 and two power amplifiers 10 and 11.

Each of the two signal sources 5 and 6 is a signal generator. The signal sources 5 and 6 output to the adder 7 two signals for transmitting acoustic waves from the transducers 1 and 2, corresponding to transmission frequencies f1 and f2 of the acoustic primary wave. In the adder 7, the two signals are added together and a signal as a result of this addition is outputted to the gate 8.

The gate 8 is a modulation circuit. The signal modulated in the gate 8 is directly inputted to the power amplifier 10, and is inputted to the power amplifier 11 via the inverter 9. Outputs from the power amplifiers 10 and 11 are respectively supplied to the transducers 1 and 2. The two transducers 1 and 2 output acoustic primary waves phase-inverted relative to each other.

A case where the frequencies of the acoustic primary wave are 5 MHz and 6 MHz and a parametric signal of 1 MHz is produced as an acoustic secondary wave will be described by way of example by referring to the results of computation of sound fields in this case using a KZK (Khokhlov-Zabolotskaya-Kuznetsov) nonlinear differential equation.

A voltage signal S12 produced by combining two frequency components corresponding to the acoustic primary wave components f1 (e.g., 5 MHz) and f2 (e.g., 6 MHz) is applied to one transducer 1. The transducer 1 transmits acoustic compressional wave of the acoustic primary wave having the frequency components f1 and f2. The acoustic primary wave components having these frequency components mutually act one on each other in a nonlinear way as they propagate. Through this mutual action, nonlinear signals of a sum component (f1+f2=11 MHz) and a differential component |f1−f2|=1 MHz are generated. These nonlinear signals increase the sound pressure by the accumulation effect as they propagate. The sum frequency and difference frequency components produced in this way can be easily derived through the trigonometric function product-sum formula. That is, the nonlinear mutual reaction between the acoustic signal expressed by sin $\omega_1 t$ and the acoustic signal expressed by sin $\omega_2 t$ means that an acoustic wave expressed by the product sin $\omega_1 t \cdot \sin \omega_2 t$ of the two signals is newly generated. This expression is expanded by using the trigonometric function product-sum formula as shown below.

$$\sin \omega_1 t \cdot \sin \omega_2 t = \{\cos(\omega_1+\omega_2)t - \cos(\omega_1-\omega_2)t\}/2$$

Thus, the mutual action is explained by using the appearance of the sum component $(\omega_1+\omega_2)$ and the difference component $(\omega_1-\omega_2)$.

To the other transducer 2 in the pair of the transducers, a voltage signal (−S12) in phase opposition to the voltage signal S12 applied to the transducer 1 is applied. An acoustic primary wave in phase opposition to the acoustic primary wave from the transducer 1 is thereby transmitted from the transducer 2. The acoustic primary wave components having these frequency components mutually act nonlinearly one on another as they propagate. As a result, nonlinear signals of a sum component (f1+f2=11 MHz) and a differential component (|f1−f2|=1 MHz) are generated. These nonlinear signals increase the sound pressure by the accumulation effect as they propagate.

However, the acoustic primary wave signal from the transducer 2 is in phase opposition to the acoustic compressional signal from the transducer 1.

A case has been described with reference to FIG. 3 where the signal S1 from the signal source 5 having the frequency f1 and the signal S2 from the signal source 6 having the frequency f2 are formed in advance and the voltage signal S12 obtained by combining the signals S1 and S2 by means of the adder 7, and the resultant voltage signal S12 is applied to the transducers 1 and 2 through the gate 8. However, the arrangement may alternatively be such that a pair of transducers: a transducer used only to transmit the acoustic primary wave signal having the frequency f1 and a transducer used only to transmit the acoustic primary wave having the frequency f2 are provided and simultaneously driven to obtain the parametric signal. Also, the arrangement may be such that another pair of the transducers structured in the same way are provided and voltage signals in phase opposition to those applied to the former pair of transducers are applied to this pair of transducers.

Figure 4:
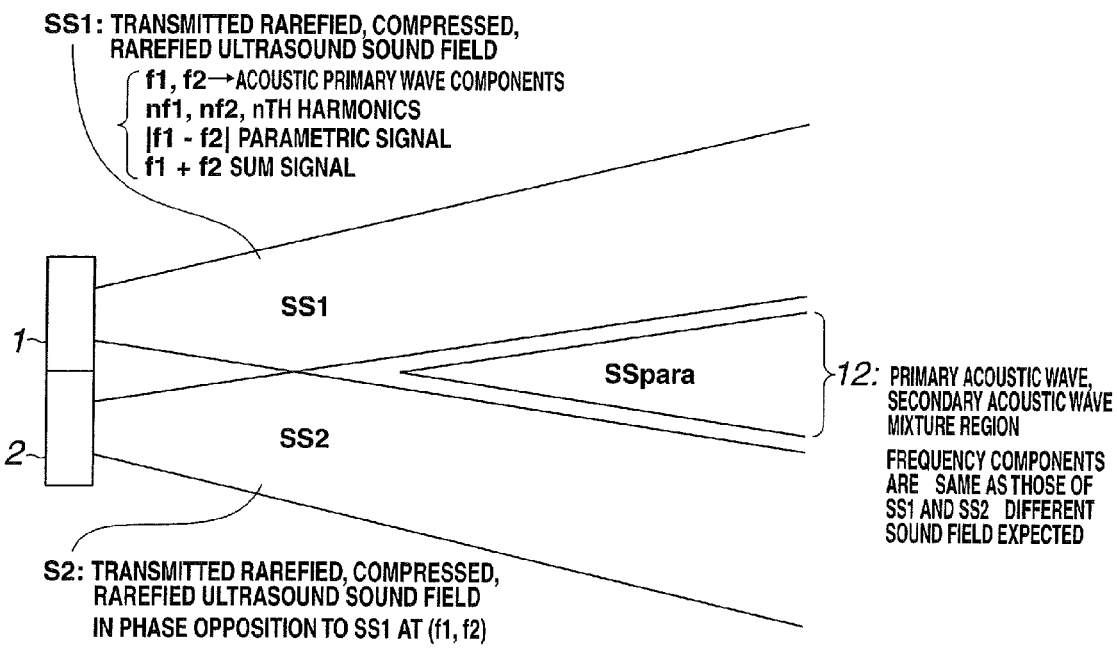
FIG. 4 is a concept diagram for explaining the formation of a specific sound field as a result of the action between the two acoustic primary waves from two regions, which are in phase opposition to each other, and each of which has frequency components f1 and f2, according to the first embodiment of the present invention.

FIG. 4 is a concept diagram for explaining the formation of a specific sound field as a result of the action between the two acoustic primary waves from the two regions, which are in phase opposition to each other, and each of which has the frequency components f1 and f2.

Referring to FIG. 4, in each of regions SS1 and SS2 of the acoustic waves outputted from the two diaphragms of the transducers 1 and 2, not only are the acoustic primary waves f1 and f2 included, but also the parametric signal (frequency |f1−f2|), harmonic components (frequencies nf1, nf2 (n: an integer equal to or larger than 2)) and a sum sound (frequency (f1+f2)) are formed. In the regions SS1 and SS2, signals formed as the sums of the harmonic components and the differences between the harmonic components are also generated. However, the sound pressure levels of these signals are much lower than those of the parametric signal and the harmonic signals. Therefore these sum and difference signals are negligible.

Figure 5:
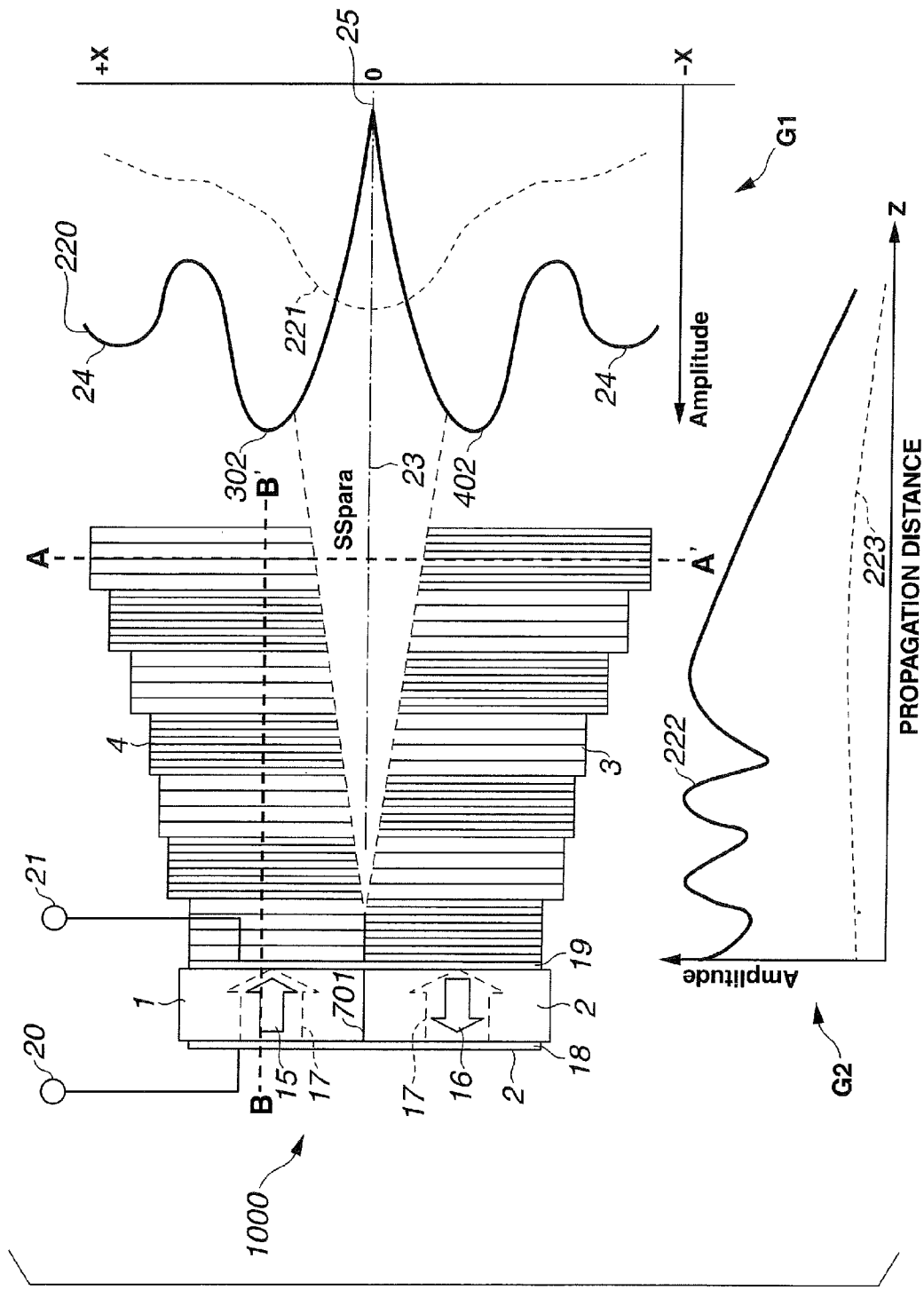
FIG. 5 is a diagram for explaining sound fields in the vicinity of a region SSpara according to the first embodiment of the present invention.

In a region SSpara where the regions SS1 and SS2 respectively formed as sound fields intersect each other, a specific sound field is formed. In this specific region SSpara where primary wave and secondary wave signals exist mixedly, no acoustic primary wave sound field is formed. FIG. 5 schematically shows the state of this sound field.

Figure 6:
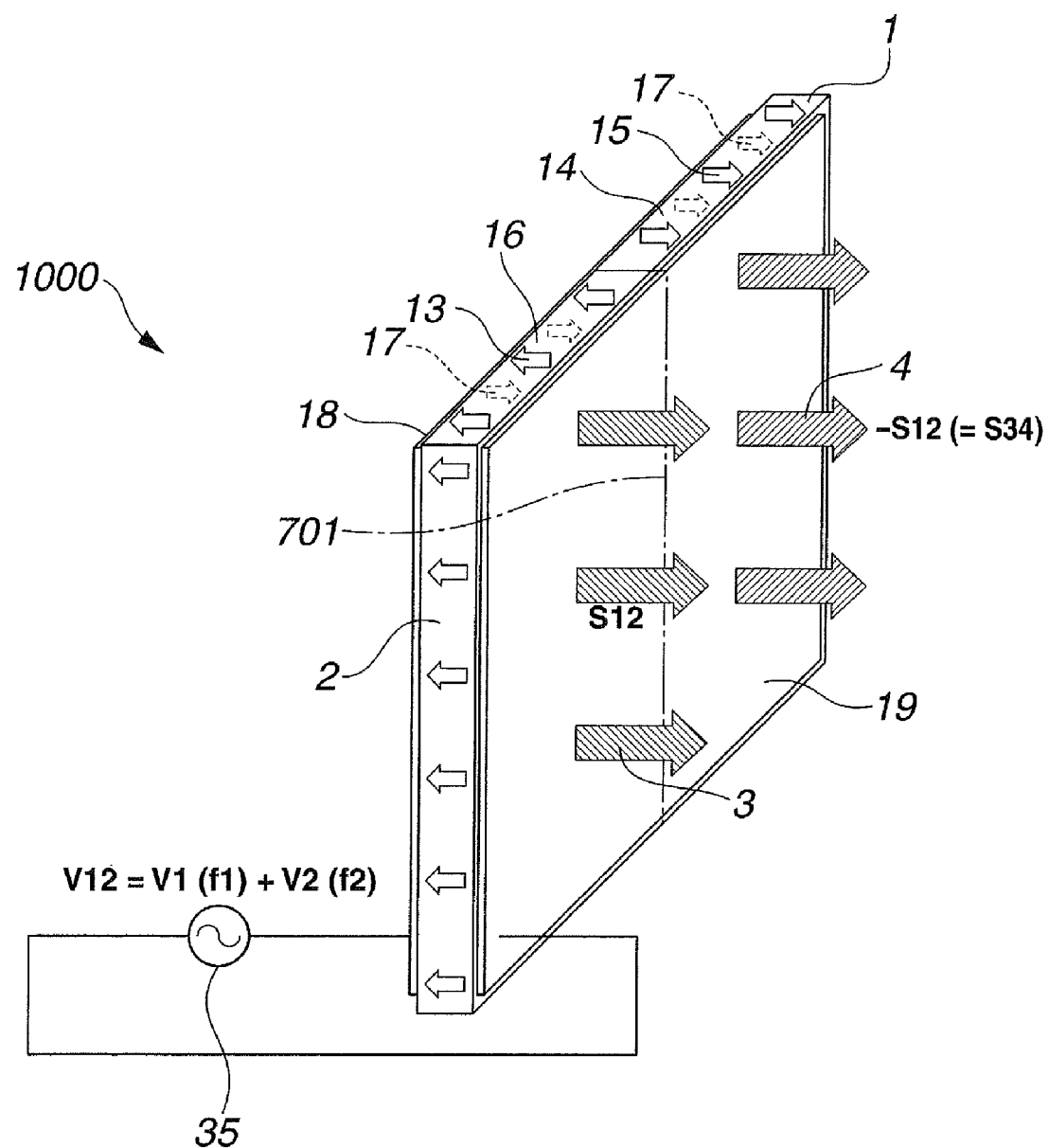
FIG. 6 is a schematic perspective view for explaining the structure of the transmitting portion shown in FIG. 5 according to the first embodiment of the present invention.

FIG. 5 is a diagram for explaining the sound fields in the vicinity of the region SSpara. FIG. 5 also shows an example of the structure of a transmitting portion of the acoustic transducer as means for generating acoustic primary waves in the mutually inverted relationship. FIG. 6 is a schematic perspective view for explaining the structure of the transmitting portion 1000 shown in FIG. 5.

Two elements provided as the transducers 1 and 2 form one piezoelectric transducer in the form of a plate. The directions of polarization 15 and 16 in the transducers 1 and 2 are set opposite to each other while being defined on opposite sides of a central boundary 701, as shown in FIG. 5. Common electrodes 18 and 19 are formed on the entire front and rear surfaces of the two transducers 1 and 2 so that the two regions formed by the two transducers 1 and 2 in the form of a plate are sandwiched between the common electrodes 18 and 19. A voltage signal from an alternating current signal source 35 is applied between terminals 20 and 21 respectively connected to the two electrodes 18 and 19. When the voltage signal is applied, and when the direction of an electric field 17 corresponds to the polarization direction 15 in the region of the transducer 1, the direction of the electric field 17 is opposite to the polarization direction 16 in the region of the transducer 2.

When the two transducers 1 and 2 are manufactured, a piezoelectric plate is prepared, for example, with an electrode in plate form formed on the entire area of each of the two surfaces, and is polarized through the entire surfaces. The prepared one piezoelectric plate is divided into two pieces, one of which is flipped and jointed by its cut surface to the other with an adhesive or like means. The joined two piezoelectric plates are wired by means of an electroconductive paste or the like so that the electrodes disposed on the same side are equipotential to each other. In this way, the two transducers 1 and 2 can be manufactured as one transducer in plate form. Needless to say, the transducers 1 and 2 may be manufactured by a different method, e.g., a method of dividing one of two electrodes of one piezoelectric element into two, polarizing the piezoelectric element while changing the polarity, and thereafter wiring the divided electrodes by sputtering or by using an electroconductive resin.

Consequently, when the transducer 1 expands to generate a compression wave, the transducer 2 contracts to generate an expansion wave. Thus, the transducers 1 and 2 can transmit acoustic primary waves in phase opposition to each other. Also, when an ultrasound enters the piezoelectric transducer having this structure, charges with opposite polarities respectively generated on the electrodes on the polarized regions with piezoelectric effect are neutralized through the electrodes 18 and 19 each formed over the two regions, so that no voltage signal is generated. Thus, even when the transducers 1 and 2 receive acoustic primary waves, they have no voltage output. That is, the piezoelectric transducer having this structure transmits acoustic primary waves in phase opposition to each other but produces no signal output at the time of receiving.

Referring to FIG. 5, acoustic primary waves outputted from the transmitting portion 100 of the parametric acoustic transducer are expressed by rarefaction and compression. Graph G1 shows the radial sound pressure intensity (beam pattern) of the acoustic primary waves and the acoustic secondary wave along line A-A'. Graph G2 shows in a modeling manner the sound pressure of the acoustic primary wave along line B-B' and the sound pressure of the acoustic secondary wave with respect to the distance along a center axis 23 passing through the boundary 701 between the two transducers 1 and 2.

In graph G1, graph 220 is a beam pattern of the acoustic primary waves having sound pressure maximum points 302 and 402. The maximum points 302 and 402 at peaks are maximum values that appeared due to an abrupt depression in sound pressure on the center axis 23. Graph 221 (dotted line) is a beam pattern of the acoustic secondary wave, i.e., a parametric sound field.

In the beam pattern of the acoustic primary waves, a region 25 where the sound pressure decreases abruptly about the center axis 23 exists, and a sidelobe 24 is formed.

In contrast, as indicated by dotted line 223 in graph G2 of FIG. 5, the parametric signal as the acoustic secondary wave is low in pressure level as a whole and has a smaller attenuation along the propagation axis direction in comparison with the acoustic primary wave indicated by the solid line. The acoustic secondary wave has the beam pattern 221 in which the sound pressure is maximized on the center axis 23. In the region SSpara, for example, the ratio of the sound pressure of the parametric signal to the sound pressure of the acoustic primary wave as an unnecessary ultrasound in parametric imaging, i.e., the acoustic primary wave, is suppressed. As a result, the S/N ratio is maximized.

Figure 7:
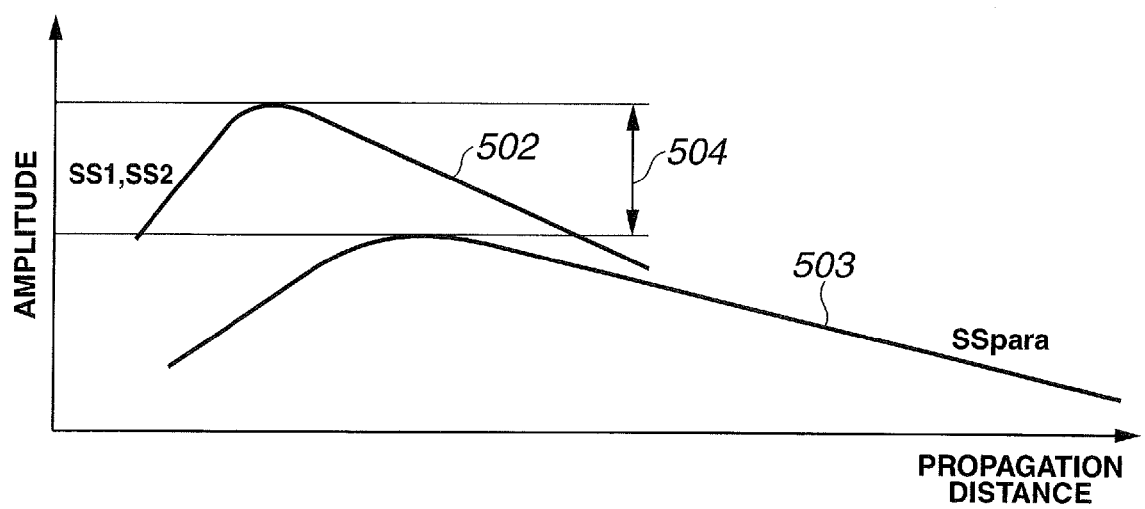
FIG. 7 is a graph showing the sound pressure distributions of the acoustic primary wave and the acoustic secondary wave in the propagation axis direction according to the first embodiment of the present invention.

FIG. 7 is a graph showing the sound pressure distributions of the acoustic primary wave and the acoustic secondary wave in the propagation axis direction. In FIG. 7, the sound pressure distribution 502 of the acoustic primary wave and the sound pressure distribution 503 of the parametric signal are compared and characteristics thereof are shown by being emphasized. From the comparison between these two sound fields, it can be understood that the sound field of the parametric signal has, in comparison with the sound field of the acoustic primary wave, (1) a remoter focal point, (2) a smaller attenuation in sound pressure on the far side of the focal point, and (3) substantially no fluctuations in sound pressure in a nearer region than the focal point. A difference 504 between the peak sound pressure levels is shown in FIG. 7.

Figure 8:
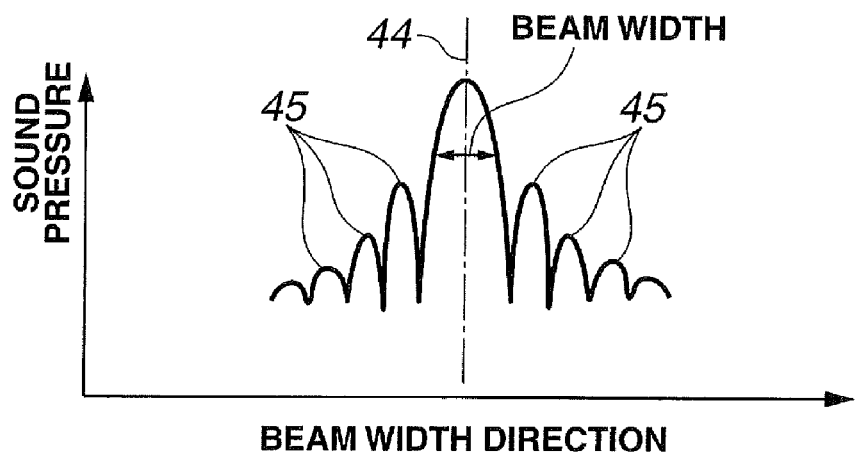
FIG. 8 is a graph showing the sound fields of 6 MHz acoustic primary waves in the beam width direction at a distance of 100 mm from the sound source when the acoustic primary waves were driven in phase with each other, according to the first embodiment of the present invention.
Figure 9:
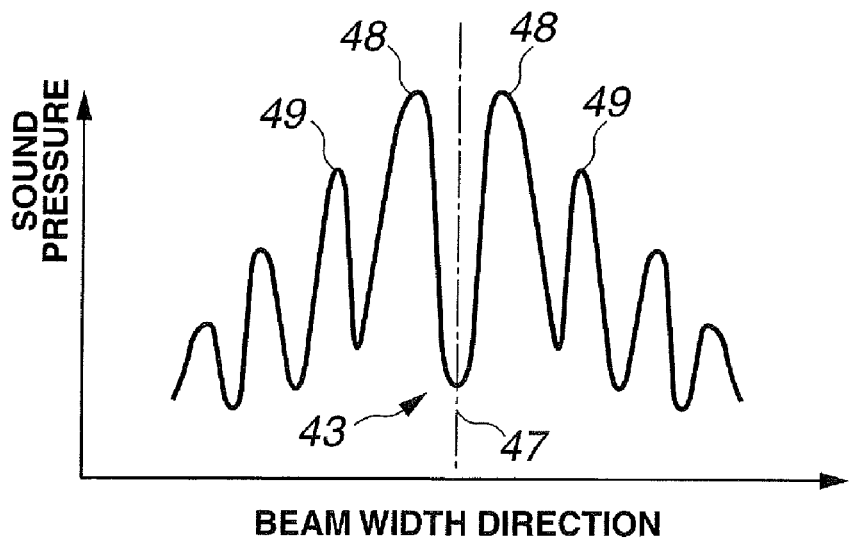
FIG. 9 is a graph showing the sound fields of 6 MHz acoustic primary waves in the beam width direction at a distance of 100 mm from the sound source when the acoustic primary waves were driven in phase opposition to each other, according to the first embodiment of the present invention.
Figure 10A:
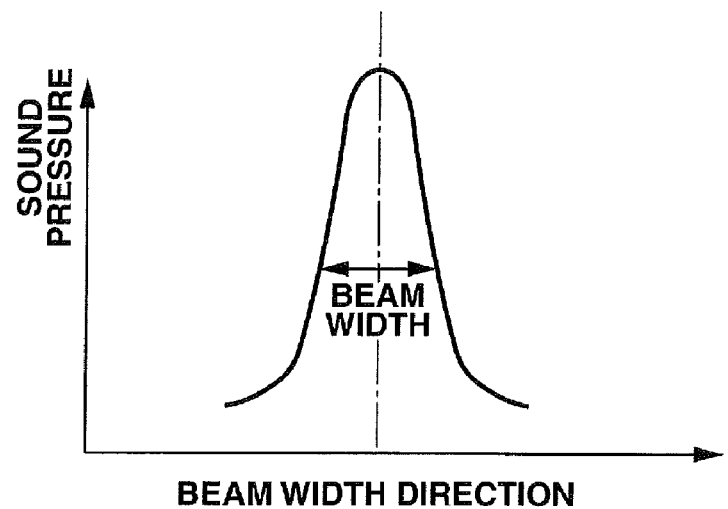
FIG. 10a is a graph showing the sound field of a 1 MHz acoustic secondary wave in the beam width direction at a distance of 100 mm from the sound source according to the first embodiment of the present invention.
Figure 10B:
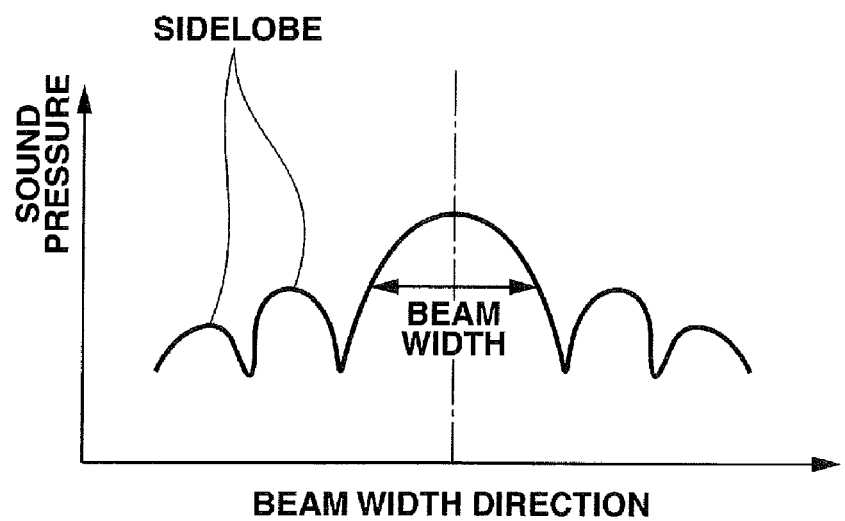
FIG. 10b is a graph showing the sound field in the beam direction of a fundamental wave having the same frequency as that of the acoustic secondary wave.

FIGS. 8 to 10 are graphs showing the sound pressures of the acoustic primary wave and the acoustic secondary wave as a result of simulation of the sound fields when the sound source frequency was set to 6 MHz in the structure of the transmitting portion described above. Substantially the same sound field patterns are formed in the case of setting to 5 MHz. FIG. 8 is a graph showing the sound fields of the 6 MHz acoustic primary waves in the beam width direction at a distance of 100 mm from the sound source when the acoustic primary waves were driven in phase with each other. FIG. 9 is a graph showing the sound fields of the 6 MHz acoustic primary waves in the beam width direction at a distance of 100 mm from the sound source when the acoustic primary waves were driven in phase opposition to each other. FIG. 10a is a graph showing the sound field of the 1 MHz acoustic secondary wave in the beam width direction at a distance of 100 mm from the sound source. FIG. 10b is a graph showing the sound field in the beam direction of a fundamental wave having the same frequency as that of the acoustic secondary wave.

From comparison between the two in FIGS. 8 and 9, it can be understood that there is a large difference between the sound fields on center axes 44 and 47, and that the sound field in the case of opposite-phase drive in the sound field in the case of in-phase drive has a region 43 where the sound pressure is minimized, that is, the acoustic primary waves are suppressed. In contrast, in the sound field of the acoustic secondary wave, i.e., the parametric signal (frequency 1 MHz), the sound pressure is not suppressed on the center axis in either of the sound field in the case of in-phase drive and the sound field in the case of opposite-phase drive, as shown in FIG. 10a; a peak of the sound pressure is exhibited on the center axis. Further, in contrast with a fundamental wave of the same frequency (1 MHz) shown in FIG. 10b, the parametric signal has such characteristics that no sidelobe appears and the beam width is reduced.

In the present embodiment, from the results shown above, the acoustic transducer described below is used to suppress the sound pressure of the acoustic primary wave, and a sound field region in which the acoustic secondary wave (parametric signal) is maximized is employed.

In the case of application of the parametric signal to an imaging technique, a better result is obtained if the down-shift ratio (DSR=(f1+f2)/2fpara where f1 and f2 represent the two frequencies of the acoustic primary wave and fpara represents the parametric signal) is higher. Therefore, obtaining fpara=1 MHz by f1=10 MHz and f2=11 MHz is preferable to obtaining fpara=1 MHz by f1=3 MHz and f2=4 MHz. However, the acoustic secondary wave is a wave that appears only when the acoustic primary wave exists, and that is influenced by attenuation of the acoustic primary wave. Therefore, the most advantageous characteristic of the parametric signal in terms of penetration depths cannot be fully utilized if the frequency of the acoustic primary wave is excessively high. Consequently, it is preferable to set DSR to about 4 to 5.

Another configuration of the transmitting portion will be described.

Figure 11:
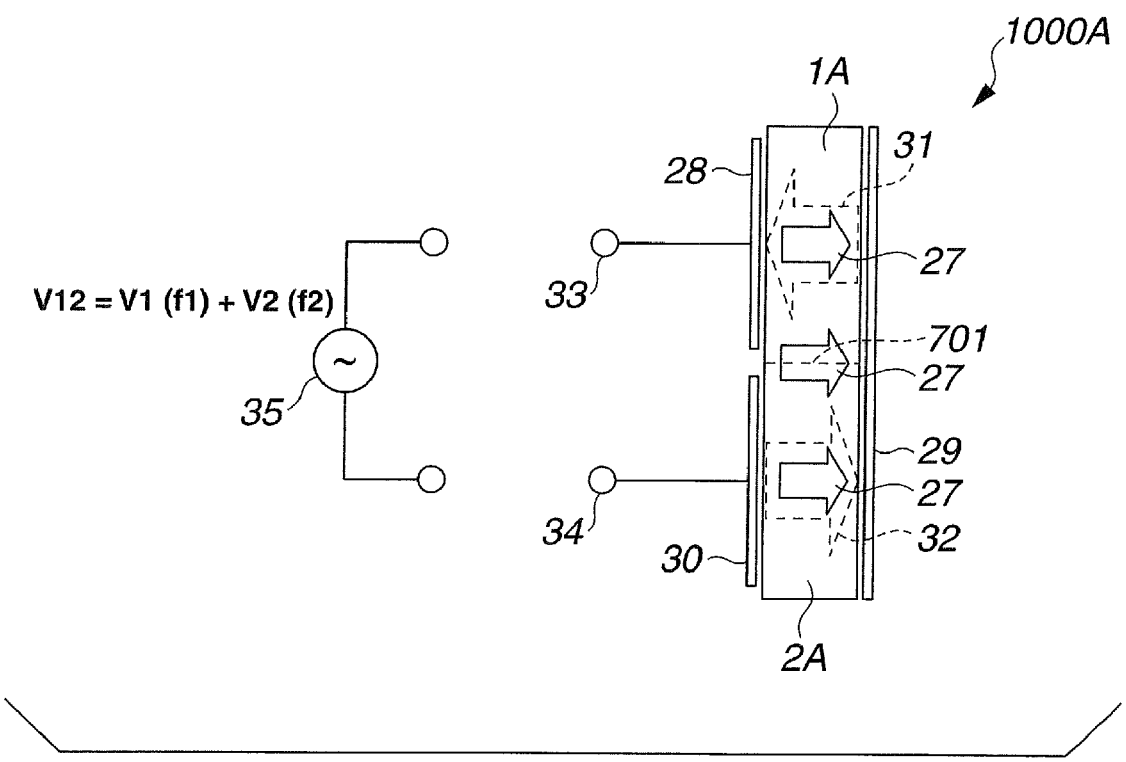
FIG. 11 shows another example of the structure of a transmitting portion of an acoustic transducer as means for generating acoustic primary waves in the mutually inverted phase relationship, according to the first embodiment of the present invention.

FIG. 11 shows another example of the structure of a transmitting portion 1000 of an acoustic transducer as means for generating acoustic primary waves in the mutually inverted phase relationship.

In the transmitting portion 1000A, each of two transducers 1A and 2A is constituted by a piezoelectric transducer in plate form. As shown in FIG. 11, the directions of polarization 27 correspond to each other. A common electrode 29 is formed on the entire area of the surfaces of two transducers 1A and 1B on one side of the same. Electrodes 28 and 30 are respectively formed on the surfaces of the transducers 1A and 1B on the other side. A voltage signal from an alternating current signal source 35 is applied between terminals 33 and 34 respectively connected to the two electrodes 28 and 30.

The transducers 1A and 2A formed of a pair of piezoelectric transducers equal in area and thickness to each other and provided with polarization 27 in the same direction as shown in FIG. 11 are prepared. Two electrodes are provided, one of which is formed as an entire-surface electrode 29 and the other of which is divided into two electrodes 28 and 30. Between the terminals 33 and 34 respectively connected to the electrodes 28 and 30, a drive signal containing frequency components f1 and f2 is applied from the drive source 35. An electric field direction 32 between the electrodes 30 and 29 and an electric field direction 31 between the electrodes 29 and 28 are thereby set opposite to each other, so that acoustic primary waves produced in phase opposition to each other and each containing the frequency components f1 and f2 are transmitted. Also, even in the event of mechanical resonance with an acoustic wave having the same frequency components at the time of receiving, no reception voltage is generated between the terminals 33 and 34.

Still another configuration of the transmitting portion will be described.

Figure 12:
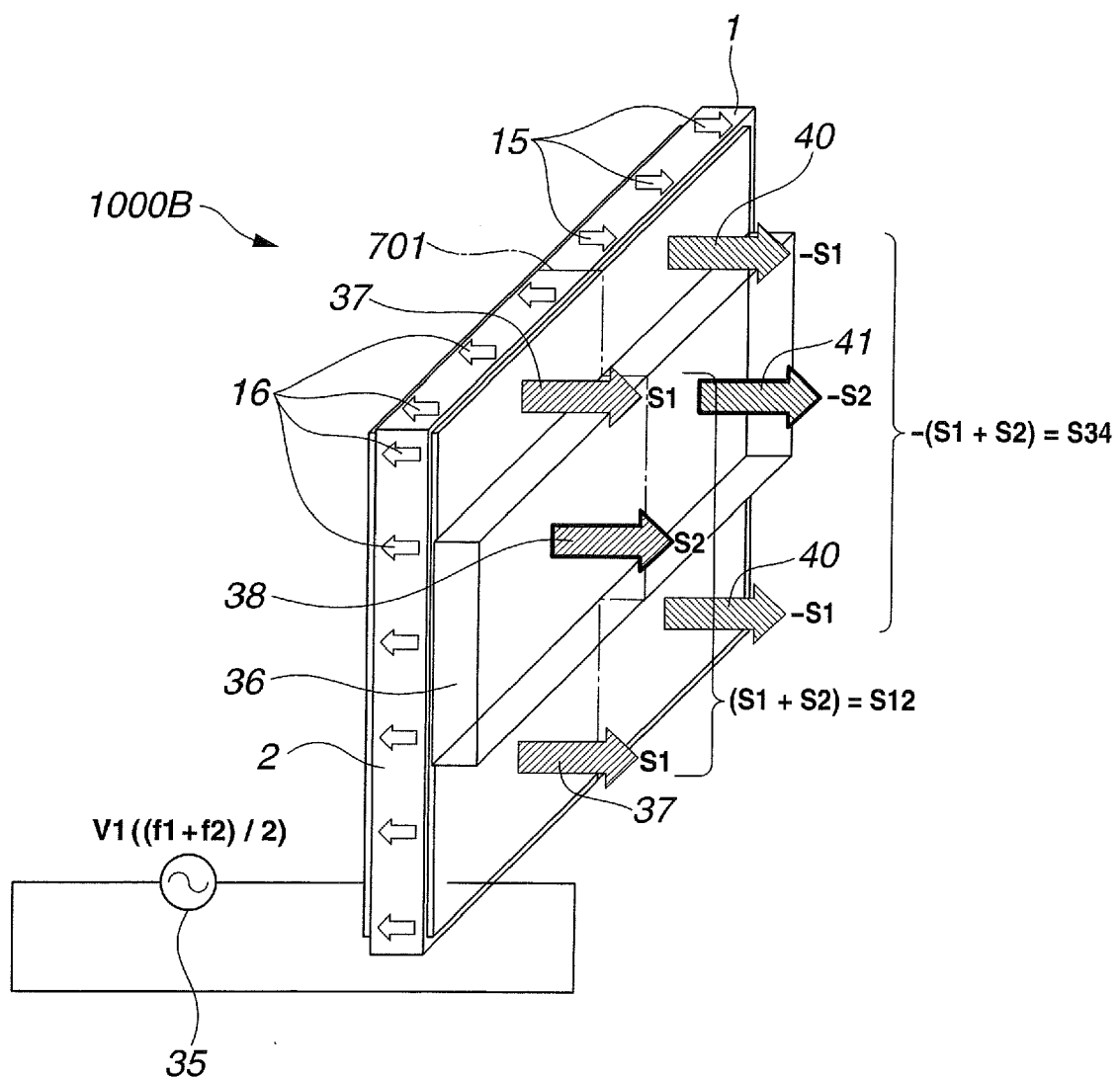
FIG. 12 is a schematic perspective view for explaining the structure of a transmitting portion relating to another configuration, according to the first embodiment of the present invention.

FIG. 12 is a schematic perspective view for explaining the structure of a transmitting portion 1000B relating to another configuration.

As shown in FIG. 12, the polarization directions 15 and 16 and the electrodes 18 and 19 forming structure in piezoelectric transducers 1 and 2 are the same as those in the configuration of the transmitting portion shown in FIGS. 5 and 6. The transducers 1 and 2 are formed of two regions with the polarization directions inverted relative to each other. From the transducers 1 and 2, acoustic primary waves 37 and 38, and 40 and 41 formed of ultrasound signals in phase opposition to each other are transmitted by applying a voltage signal having a frequency of (f1+f2)/2 as a center frequency. Points of difference from the configuration shown in FIG. 5 reside in that a frequency-reducing plate 36 is joined to the front surfaces or the rear surfaces of the transducers 1 and 2 (to the front surfaces in FIG. 12), and that in the example shown in FIG. 12 the voltage signal from a drive source 35A for generating acoustic primary waves has a frequency component which is a single signal V1 having a single center frequency (f1+f2)/2. The single signal V1 is, for example, a wide-band pulse such as a burst wave or a spike wave.

The frequency-reducing plate 36 provided as a frequency-reducing member is an elastic member in the form of a plane-parallel plate made of the same material as the piezoelectric material. For example, if the transducers 1 and 2 are PZT ceramic, a PZT ceramic thin plate is bonded to form the frequency-reducing plate 36, or a PZT thick film is formed by an aerosol deposition method or like means. In place of the PZT thick film, a resin film having certain hardness may be formed by applying the material or by a method of forming by bonding and setting. For example, 6 MHz acoustic primary waves from the transducers 1 and 2 can be realized by using thickness longitudinal vibration through a thickness of 0.33 mm. To obtain a 5 MHz thickness longitudinal vibration, a 0.07 mm thick PZT ceramic thin plate may be bonded so as to obtain a total thickness of 0.4 mm while covering the same areas on the two regions having the polarization directions 15 and 16, or a corresponding thick film may be formed. As a drive signal, a pulse signal formed of a single frequency component having a frequency of (f1+f2)/2 may be driven. Transmission of acoustic primary waves having frequencies f1 and f2 and in phase opposition to each other (expressed by S1+S2=S12 and −(S1+S2)=S34) from the transmitting portion 1000B is thus enabled.

The above-described method of using a frequency-reducing plate is not exclusively used as a method of generating resonance frequencies from one piezoelectric transducer. For example, a vibration at an increased frequency can be obtained from a portion of the surface of one piezoelectric transducer by forming a region reduced in thickness relative to the other region in the piezoelectric transducer, e.g., a recessed portion.

A transmitting and receiving parametric acoustic transducer including a receiving portion will next be described.

Figure 13:
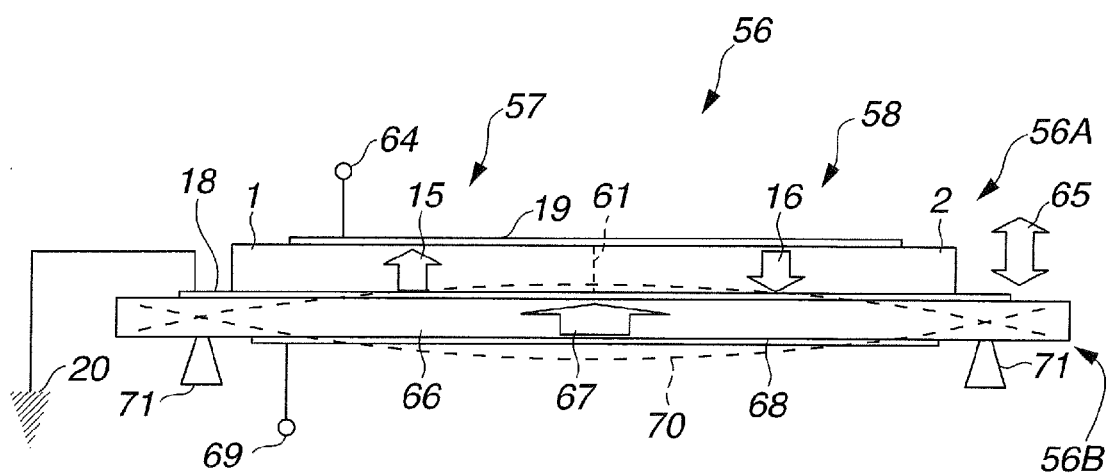
FIG. 13 is a cross-sectional view showing the configuration of a transmitting and receiving parametric acoustic transducer according to the first embodiment of the present invention.

FIG. 13 is a cross-sectional view showing the configuration of a transmitting and receiving parametric acoustic transducer (hereinafter referred to as "parametric acoustic transducer) 56 according to the present embodiment. The parametric acoustic transducer 56 is configured by including a transmitting portion 56A and a receiving portion 56B.

The transmitting portion 56A has the same configuration as that of the transmitting portion 1000 shown in FIG. 5. The transmitting portion 56A may alternatively have the same configuration as that shown in FIG. 11 or FIG. 12.

The transmitting portion 56A has regions 57 and 58 corresponding to the two transducers 1 and 2 that transmit acoustic primary waves. The two transducers 1 and 2 generate vibration along acoustic primary wave propagation direction, i.e., thickness longitudinal vibration 65, for the generation of acoustic primary waves. That is, the transmitting portion 56A in plate form is a piezoelectric-type thickness longitudinal transducer having the regions 57 and 58 in which the two transducers 1 and 2 are made to excite piezoelectric-type thickness longitudinal vibration 65 to transmit longitudinal ultrasounds (acoustic primary waves) from their surfaces.

On the other hand, the receiving portion 56B includes a piezoelectric-type transducer 66 in plate form laminated on and joined to the transmitting portion 56A. The transducer 66 in plate form is supported at two peripheral positions, more specifically, by two supporting members 71 along two side portions so as to be capable of vibrating in a bending vibration manner as a whole. That is, the receiving portion 56B in plate form is the transducer 66 capable of bending vibration.

As described above, the transmitting portion 56A is divided into the two regions 57 and 58; the electrodes 18 and 19 are formed on the entire areas of the front and rear surfaces of the transducers 1 and 2; and the polarization directions 15 and 16 are set opposite to each other while being defined on opposite sides of a boundary 61. To receive a reflected wave of an acoustic secondary wave generated with propagation of acoustic primary waves, the receiving portion 56B is disposed so that its region for receiving the reflected wave is superposed on the transducers 1 and 2 of the transmitting portion 56A as seen from a position in the direction of transmission of acoustic primary waves.

As shown in FIG. 6, the transmitting portion 56A is divided into two regions having polarization directions opposite to each other, the electrodes 18 and 19 are formed on the entire areas of the front and rear surfaces, and the electric field 17 is applied uniformly through the entire surface in the same direction. If the thickness of the transmitting portion 56A is t and the longitudinal wave velocity is v1, the resonance frequency in this case is expressed by v1/2t with respect to each of the polarized regions. By the same drive signal, piezoelectric vibrations are excited with the same amplitude and in phase opposition to each other respectively from polarized regions 13 and 14. Also, acoustic primary waves 3 and 4 transmitted from the surfaces have phases S12 and −S12 opposite to each other.

When a voltage signal V12 obtained by combining voltage signals V1 (f1) and V2 (f1) in the band of the transducers 1 and 2 is applied between electric signal input terminals 20 and 64 (terminal 20 is grounded in FIG. 13), acoustic primary waves having the two frequency components f1 and f2 are transmitted.

With propagation of the acoustic primary waves 3 and 4, nonlinear acoustic secondary waves, such as harmonics nf1 and nf2, a differential signal (parametric signal), a sum signal, and sum and difference signals of the harmonics, in addition to the acoustic primary waves, are propagated based on the nonlinearity of the propagation medium to form their respective sound fields. Each of the difference and sum signals as parametric signals is usable. In the present embodiment, the difference signal is used.

No description will be made of the sum signal since the sum signal can be used by the same method. However, the sum signal can be obtained as high-resolution signal because of its high frequency, such that a high-resolution image can be obtained at the time of imaging with the signal.

These acoustic signals are reflected at an acoustic impedance boundary not shown in the figure and are received as echo signals by the piezoelectric element transducer 66 in the receiving portion 56B. The polarization direction 67 of the transducer 66 in the receiving portion 56B may be selected as any one of the two directions. Further, the receiving portion 56B has such a transducer structure as to resonate selectively with the desired one of the various acoustic signals described above.

More specifically, in the transducer 66, bending vibration 70 such as indicated by dotted lines in FIG. 13 is caused. For example, in a case where f1=5 MHz, f2=6 MHz and fpara=1 MHz are selected to set the DSR to about 5, the specific bandwidth of is (f2−fpara)/(f2+fpara)/2=1.4, i.e., 140% or more. If instable regions where changes in phase at band ends are large are avoided, it is preferable to increase the specific band width by 20% to about 170% by increasing by 20%.

As shown in FIG. 13, the parametric acoustic transducer 56 is a bimorph structure in which two divided transducers 1 and 2, provided as the transmitting portion 56A, and the piezoelectric transducer 66 in a uniformly polarized state, provided as the receiving portion 56B, are joined together. In the receiving portion 56B, the transducer 66 uniformly polarized is formed on the electrode 18 side and an electrode 68 is formed on the entire surface opposite from the electrode 18 in contact with the transducer 66. The electrode 18 serves as a common electrode for the piezoelectric transducers 1, 2, and 66. That is, the parametric acoustic transducer 56 is configured by bonding the transmitting portion 56A and the receiving portion 56B together, as shown in FIG. 13.

The parametric acoustic transducer 56 is configured by being supported by the supporting members 71. If the combined thickness is t1 and the distance between the supporting members 71 is L, a resonance frequency fbend of this bimorph piezoelectric transducer is $$fbend=0.453(t1/L^2)SQRT(Y/\rho)$$

where Y is the Young's modulus of the bimorph constituent material and ρ is the density.

As described above, the receiving portion 56B vibrates in a bending vibration manner in response to the low frequency of the parametric signal to output a received signal.

It is, therefore, possible to easily adjust the resonance frequency to the desired value by adjusting the thickness of the transducer 66 in the combined thickness t1 or the distance between the supporting portions 71.

In the case shown in FIG. 13, a circuit not including the inverter 9 shown in FIG. 3, i.e., a circuit not requiring branch wiring, suffices for the drive signal to the parametric acoustic transducer 56, and only one of the power amplifiers 10 and 11 suffices.

The received signal is outputted through the terminal 69 of the transducer 66 shown in FIG. 13.

For example, the parametric acoustic transducer according to the present embodiment can be used for image forming, i.e., imaging of a tomographic image or the like, by arranging a plurality of the above-described parametric acoustic transducers 56 and performing scanning with the transducers. In such a case, output signals are inputted to an ordinary receiving circuit, undergo processings including amplification, filtering, and the like and are converted into a video signal, thereby displaying an image on a monitor.

While the transmitting portion 1000 shown in FIG. 5 is attached to the receiving portion 56B in the structure of the parametric acoustic transducer 56 shown in FIG. 13, the parametric acoustic transducer 56 may alternatively have a structure in which the transmitting portion 1000B shown in FIG. 11 is attached to the receiving portion 56B as mentioned above.

An example of a parametric acoustic transducer having a transmitting portion a configuration using the frequency-reducing plate described above with reference to FIG. 12 will next be described.

Figure 14:
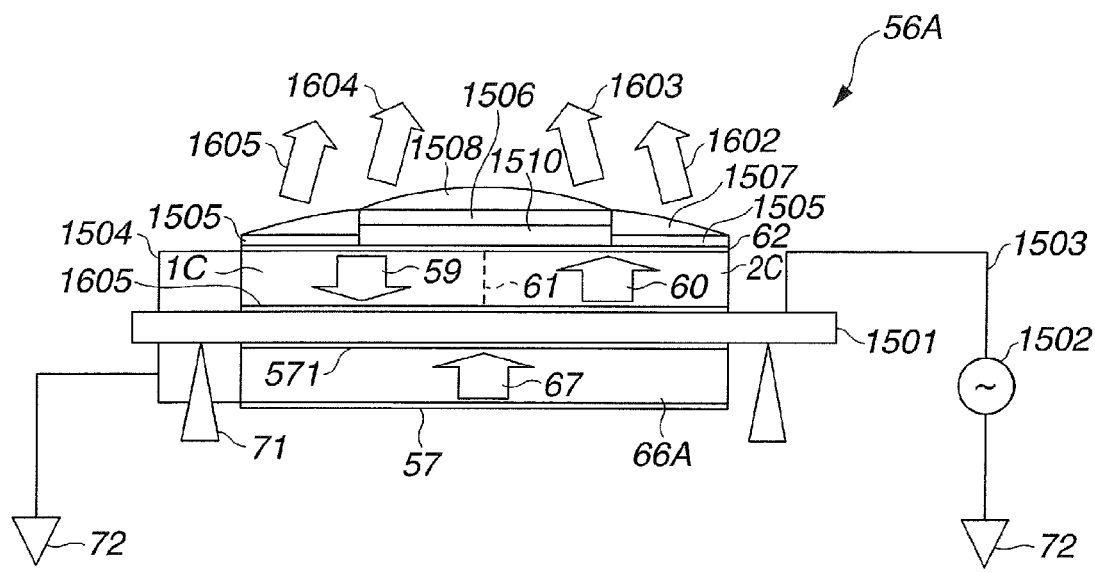
FIG. 14 is a cross-sectional view of a parametric acoustic transducer having a transmitting portion configuration using a frequency-reducing plate according to the first embodiment of the present invention.

FIG. 14 is a cross-sectional view of a parametric acoustic transducer having a transmitting portion configuration using a frequency-reducing plate. The parametric acoustic transducer 56A shown in FIG. 14 is a transmitting and receiving ultrasound transducer for parametric imaging of a two-terminal structure usable in a conventional ultrasound diagnosis apparatus.

Figure 15:
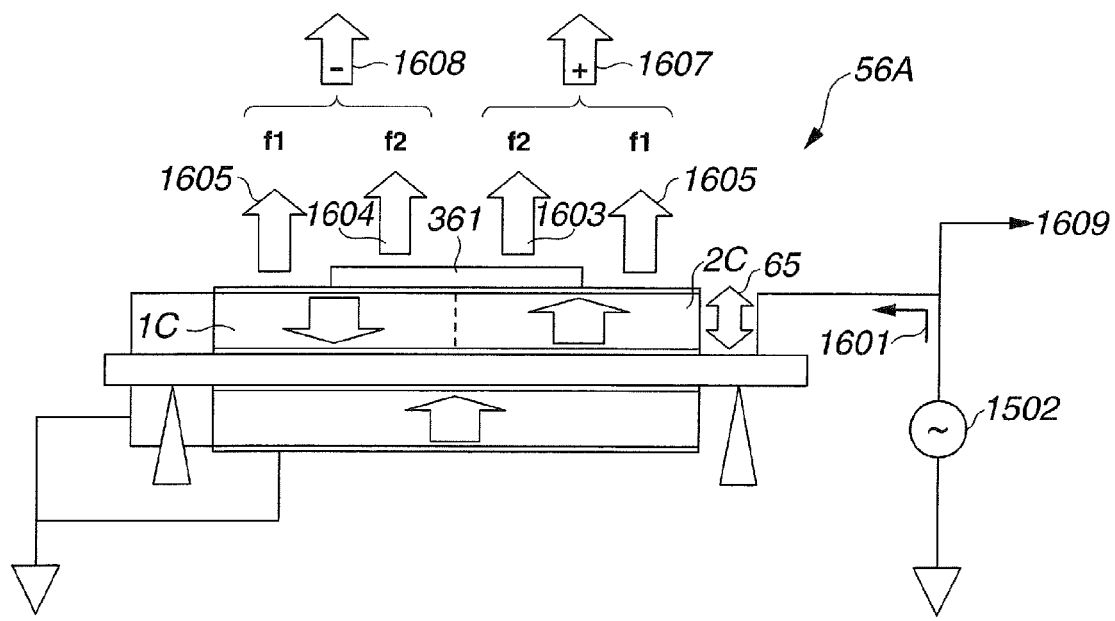
FIG. 15 is a diagram for explaining transmission of acoustic primary waves according to the first embodiment of the present invention.
Figure 16:
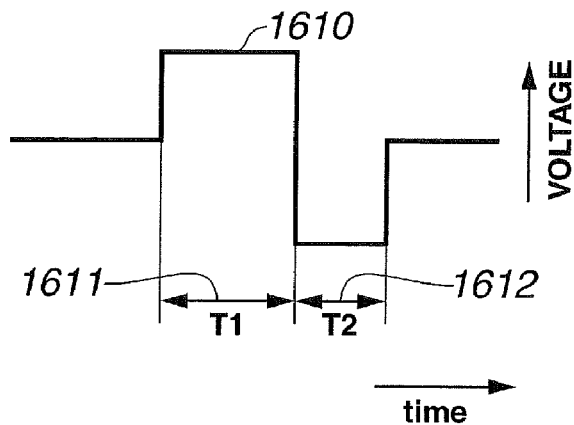
FIG. 16 is a waveform diagram of a drive pulse signal according to the first embodiment of the present invention.
Figure 17:
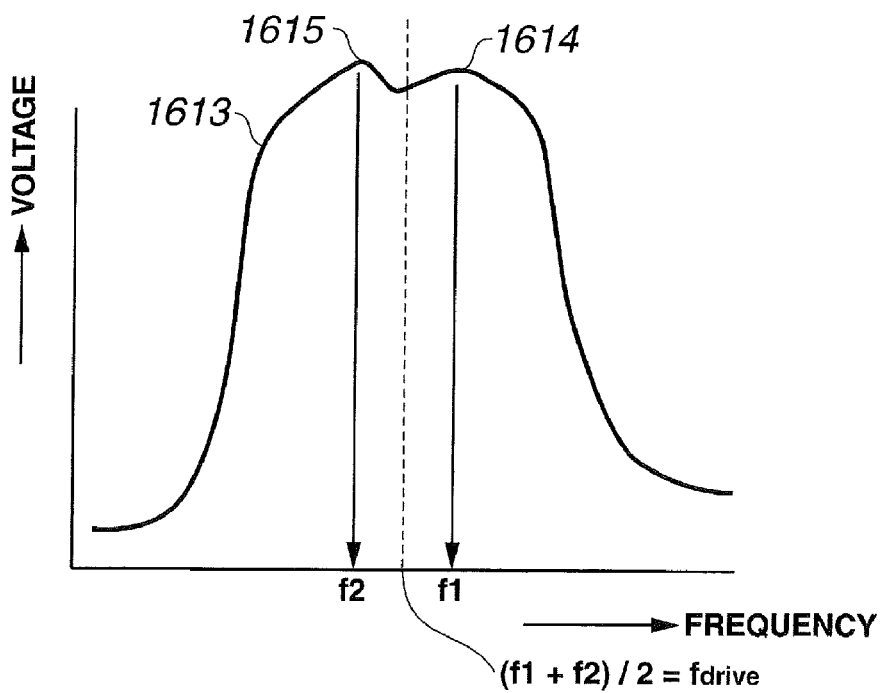
FIG. 17 is a diagram for explaining a spectrum of the drive pulse signal according to the first embodiment of the present invention.
Figure 18:
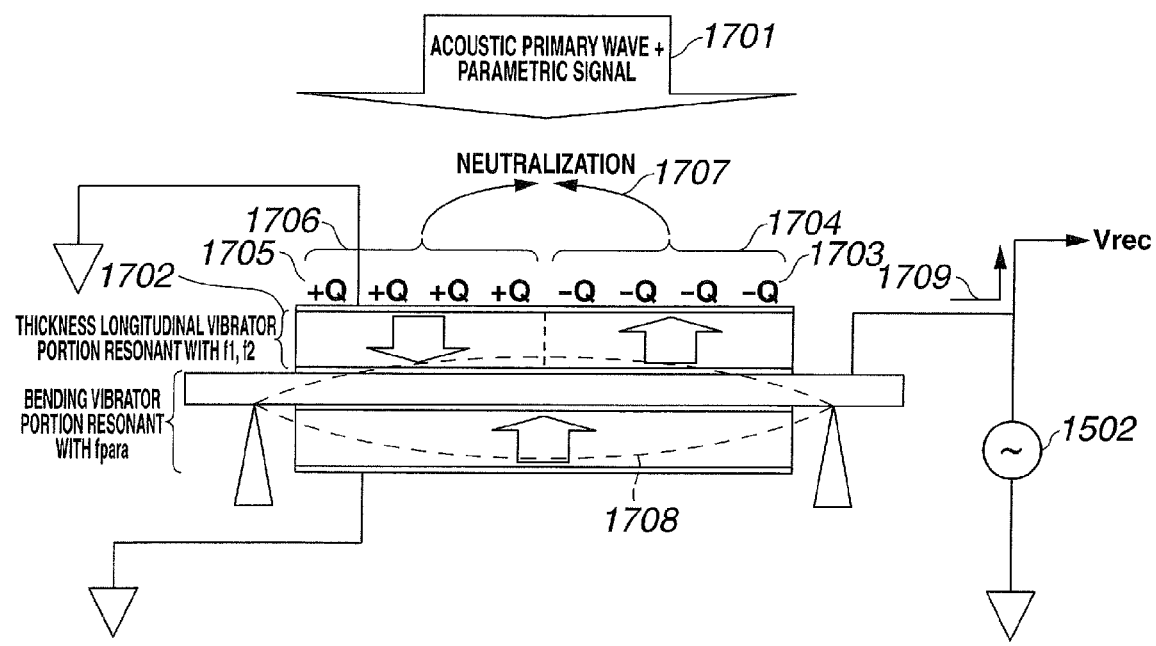
FIG. 18 is a diagram for explaining reception of an acoustic secondary wave according to the first embodiment of the present invention.

FIGS. 15 to 17 are diagrams for explaining the principle of control of transmission of acoustic primary waves with the parametric acoustic transducer 56A. FIG. 18 is a diagram for explaining the principle of control of reception of an acoustic secondary wave with the parametric acoustic transducer 56A.

The parametric acoustic transducer 56A shown in FIG. 14 is of a two-terminal structure and capable of transmitting acoustic primary wave and receiving at a high S/N a parametric signal formed of an acoustic secondary wave, as are ordinary conventional ultrasound transducers.

As shown in FIG. 14, the parametric acoustic transducer 56A has a structure in which a frequency-reducing plate 1510 is laminated on two transducers 1C and 2C. An acoustic matching layer 1506 is provided on the frequency-reducing plate 1510. An acoustic lens 1508 is provided on the acoustic matching layer 1506. An acoustic matching layer 1505 is also formed on each of regions of the transducers 1C and 2C not covered with the frequency-reducing plate 1510. An acoustic lens 1507 is provided on the acoustic matching layer 1505.

The design and functions of these acoustic matching layers 1505 and 1506 and acoustic lenses 1507 and 1508 are the same as those of ordinary acoustic matching layers and acoustic lenses. Also, the methods for making these acoustic matching layers 1505 and 1506 and acoustic lenses 1507 and 1508 are the same as those for making ordinary acoustic matching layers and acoustic lenses.

The two transducers 1C and 2C are provided on an electroconductive substrate (or an insulating substrate having its surface processed so as to be electrically conductive) 1501. A drive voltage is applied from a drive source 1502 to one of two electrodes of the two transducers 1C and 2C and to one of two electrodes of the receiving transducer 66A via wiring 1503.

The other electrode of the two transducers 1C and 2C and the other electrode of the receiving transducer 66A are grounded through wiring 1504.

The principle of receiving an acoustic secondary wave at a high S/N will be described with reference to FIGS. 15 to 18. FIG. 15 is a diagram for explaining transmission of acoustic primary waves. FIG. 16 is a waveform diagram of a drive pulse signal. FIG. 17 shows a spectrum of the drive pulse signal. FIG. 18 is a diagram for explaining reception of an acoustic secondary wave.

As shown in FIG. 15, a normal-phase acoustic primary wave (frequency: f1) 1602 and a normal-phase acoustic primary wave (frequency: f2) 1603 are outputted from the transducer 2C by application of a drive signal 1601, and an opposite-phase acoustic primary wave (frequency: f2) 1604 and an opposite-phase acoustic primary wave (frequency: f1) 1605 are outputted from the transducer 1C. As a result, a normal-phase acoustic primary wave 1607 and an opposite-phase acoustic primary wave 1608 are outputted from the parametric acoustic transducer 56A.

A received parametric signal is supplied to a receiving circuit 1609.

The drive signal 1601 is a drive pulse signal 1610 such as shown in FIG. 16. The drive pulse signal 1610 is a signal having a period (T1) of a pulse width 1611, and a period (T2) of a pulse width 1612. As shown in FIG. 17, a signal spectrum 1613 of the drive signal 1610 has a peak 1614 at the frequency f1 and a peak 1615 at the frequency f2.

Accordingly, when the drive signal 1601 with the signal spectrum 1613 having peaks at the frequencies f1 and f2 is applied from the drive signal source 1502 to the parametric acoustic transducer 56A, the acoustic primary waves 1603 and 1604 having the frequency component f2 are transmitted from the regions to which the frequency-reducing plate 1510 is joined, and the acoustic primary waves 1602 and 1605 having the frequency component f1 are transmitted from the regions to which the frequency-reducing plate 1510 is not joined. As a result, the acoustic primary waves 1607 and 1608 inverted relative to each other are transmitted from the regions of the two transducers 1C and 2C formed so that the polarization directions 59 and 60 are opposite to each other.

At this time, the piezoelectric unimorph constituted by the electroconductive substrate 1501 and the transducer 66A does not resonate because the resonance frequency is extremely low in comparison with the frequencies f1 and f2.

As described above, the normal-phase acoustic primary wave and the opposite-phase acoustic primary wave having the f1 and f2 components can be simultaneously transmitted. Thus, the formation of the parametric signal can be realized based on the propagation of the acoustic primary waves having the f1 and f2 components and the acoustic nonlinearity of the ultrasound propagation medium.

The acoustic matching layers 1505 and 1506 increase the sound pressure of the acoustic primary waves to be transmitted and simultaneously reduce the pulse width, thereby contributing to an improvement in resolution in the depth direction. The acoustic lenses 1507 and 1508 converge the beams of the acoustic primary waves to improve the lateral resolution.

The received signal contains the acoustic primary waves larger in sound pressure by about 20 dB than the parametric signal, the parametric (difference) signal, the nth harmonics nf1 and nf2 of the acoustic primary waves, the parametric (sum) signal and other signals, having different frequency components. In response to the acoustic primary waves therein, thickness longitudinal resonance 65 occurs in the regions of the transducers 1C and 2C.

At this time, charges are generated on the electrode on the region of the transducers 1C and 2C, as shown FIG. 18. For example, when +charge 1705 is generated on the electrode on the region of the transducer 1C, −charge 1703 is generated on the electrode on the region of the transducer 2C.

However, the electrode on the region of the transducer 1C and the electrode on the region of the transducer 2C are included in one integral electrode and, therefore, the charges are neutralized (1707) in this electrode 19 and disappear. That is, even when any of the acoustic primary waves is received, the acoustic primary wave, including a sidelobe, is not converted into a voltage signal.

On the other hand, the parametric signal has the frequency component |f1−f2| and a design is made so that the resonance frequency of the piezoelectric unimorph formed of the electroconductive semiconductor substrate 1501 and the transducer 66A is |f1−f2|. Therefore bending resonance of the piezoelectric unimorph occurs as vibration indicated by dotted line 1708 in FIG. 18. This mechanical vibration is converted into a voltage signal 1709 by the piezoelectric effect and the voltage signal 1709 is transmitted to the receiving circuit 1609. This unimorph transducer does not resonate with signals of other frequency components mixed in the received signal. Thus, the S/N ratio of the parametric signal is largely increased.

With the above-described configuration, acoustic primary waves in phase opposition to each other are transmitted and a space region in which the acoustic primary waves can be suppressed is utilized. Also, as described with respect to the present embodiment, an arrangement in which the transducer element that resonates with a frequency component that the acoustic primary waves have and the transducer element that resonates with a frequency component that the parametric signal has are configured integrally with each other is used. In this way, parametric imaging with a high S/N ratio for example is enabled. Moreover, the depth resolution and lateral resolution are improved by the effect of addition of the acoustic matching layer and the acoustic lens.

As described above, the parametric acoustic transducer in the above-described first embodiment is configured so that the transmitting portion generates thickness longitudinal vibrations to transmit acoustic primary waves and the receiving portion receives a parametric signal by means of bending vibration.

Thus, according to the present embodiment, it is possible to realize an acoustic transducer capable of largely suppressing acoustic primary waves in receiving portion responsible, for example, for a reduction in contrast resolution which is a consideration in ultrasound imaging while making full use of the characteristic of a parametric signal that resides in limiting the attenuation and capability of long-distance propagation and the characteristic of the parametric signal that resides in having directionality much higher than that of a fundamental wave of the same frequency, and while being made simple in structure and compact.

An acoustic secondary wave generated has no sidelobe and has high directionality. Effectively receiving this acoustic secondary wave requires that the transmitting portion and the receiving portion be completely or partially superposed one on another as seen from the acoustic radiation surface side, as described above.

Second Embodiment

A second embodiment of the present invention will be described.

In the above-described first embodiment, thickness longitudinal vibration and bending vibration are utilized in the transmitting portion and in the receiving portion, respectively. The present embodiment differs from the first embodiment in that bending vibration is used in each of the transmitting portion and the receiving portion.

Figure 19:
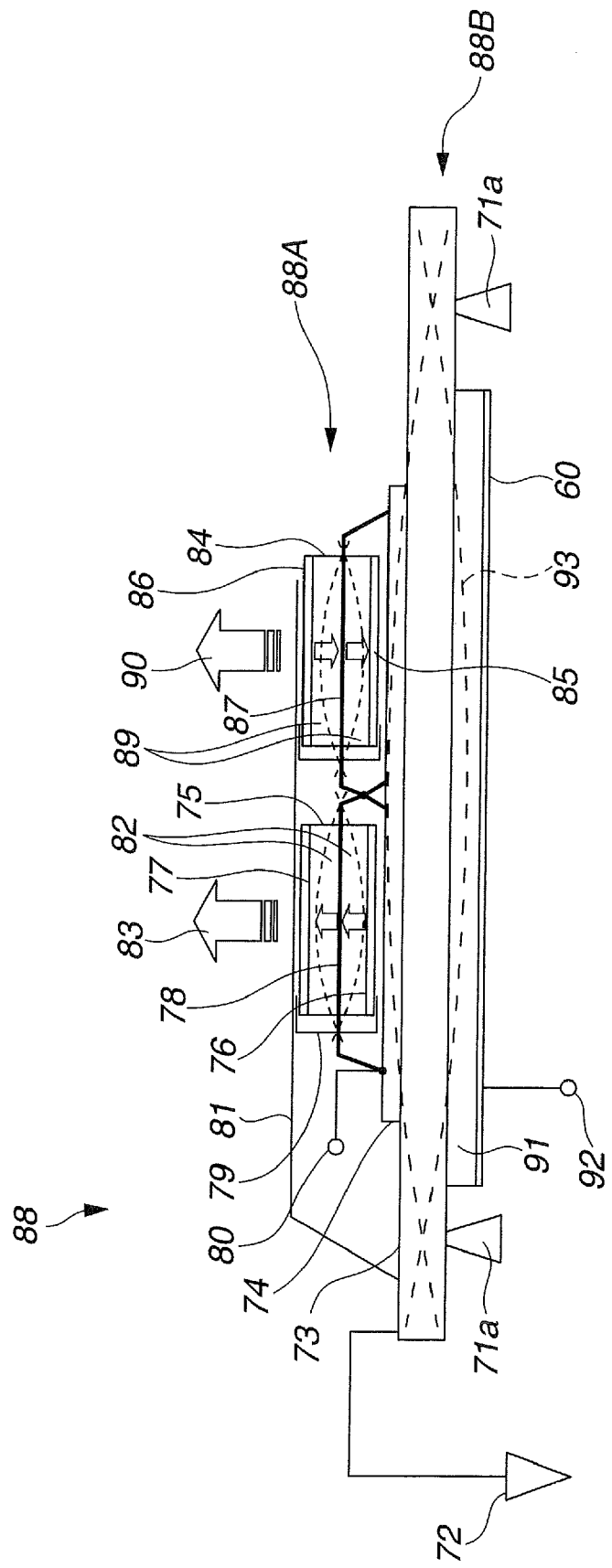
FIG. 19 is a cross-sectional view showing the structure of a parametric acoustic transducer according to a second embodiment of the present invention.

FIG. 19 is a cross-sectional view showing the structure of a parametric acoustic transducer according to the present embodiment. A transmitting and receiving parametric acoustic transducer 88 is configured by including a transmitting portion 88A and a receiving portion 88B. This parametric acoustic transducer 88 is of such a structure as to be suitably applied to a case where the frequency of an acoustic primary wave is low, for example, 100 kHz or less.

The transmitting portion 88A is configured by including two piezoelectric bimorphs 75 and 84.

The bimorphs 75 and 84 of the parametric acoustic transducer 88 respectively generate bending vibrations for transmission of acoustic primary waves.

On one of two surfaces of an electroconductive substrate 73 (upper surface in FIG. 19), an insulating film of an insulating member 74 is formed. On the other surface of the electroconductive substrate 73 on the opposite side (lower surface in FIG. 19), a piezoelectric-type transducer 91 in the form of a thin plate is formed by an adhesive or like means.

The transducer 91 has the electroconductive substrate 73 as an electrode on one side and has an electrode 60 formed over the entire surface on the other side. The electrode 60 is connected to a terminal 92. The electroconductive substrate 73 and the piezoelectric transducer thin plate 91 constitute a piezoelectric unimorph. The piezoelectric unimorph constituting the receiving portion 88B is supported by supporting members 71a at nodes in bending vibration 93. In the receiving portion 88B, to receive a reflected wave of an acoustic secondary wave generated with propagation of acoustic primary waves, a region for receiving the reflected wave is disposed so as to be superposed on the transducers in the transmitting portion 88A as seen from a position in the direction of transmission of acoustic primary waves. The receiving portion 88B is supported so as to be positioned at a predetermined distance from the transmitting portion 88A.

On the other hand, a pair of piezoelectric bimorphs 75 and 84 are disposed side by side on the upper surface side of the electroconductive substrate 73. In the piezoelectric bimorph 75, a pair of piezoelectric transducers 82 are joined together, with an electroconductive shim member 78 interposed therebetween, the pair of piezoelectric transducers 82 having polarization directions corresponding to each other. Also in the piezoelectric bimorph 84, a pair of piezoelectric transducers 89 are joined together, with an electroconductive shim member 87 interposed therebetween, the pair of piezoelectric transducers 89 having polarization directions corresponding to each other. The directions of polarization of the piezoelectric bimorphs 75 and 84 are opposite to each other.

Electrodes 76 and 77 are respectively formed on the entire areas of opposite surfaces of the piezoelectric bimorph 75. Also, electrodes 85 and 86 are respectively formed on the entire areas of opposite surfaces of the piezoelectric bimorph 84.

The piezoelectric bimorphs 75 and 84 are respectively supported by the electroconductive shim members 78 and 87 so as to have a predetermined distance from the insulating member 74. That is, the piezoelectric bimorphs 75 and 84 are spaced apart from the insulating member 74. The electrodes 76 and 77 of the piezoelectric bimorph 75 and the electrodes 85 and 86 of the piezoelectric bimorph 84 are respectively connected for electrical conduction through conduction wiring 79.

End portions of the electroconductive shim members 78 and 87 are buckled and a portion of buckled ends is fixed on an electrode pad formed on the surface of the insulating member 74 and having electrical conductivity, which electrode pad is not shown in the figure. A connection is established between the electrode pad and a terminal 80.

On the other hand, on the ground side, the electrodes 76, 77, 85, and 86 are all connected to a terminal (not shown in the figure) on the ground 72 side through a common grounding line 81 to which the electrodes are connected and further through the electroconductive substrate 73 in the present embodiment.

The pair of piezoelectric transducers 82 in the piezoelectric bimorph 75 are joined together so as to have polarization directions corresponding to each other and set uniformly upward as viewed in FIG. 19, while the pair of piezoelectric transducers 89 in the piezoelectric bimorph 84 are joined together so as to have polarization directions corresponding to each other and set uniformly downward as viewed in FIG. 19. The piezoelectric bimorphs 75 and 84 are configured in this way to vibrate in phase opposition to each other in bending vibration in response to a drive signal of the same waveform.

The two piezoelectric bimorphs 75 and 84 respectively generate bending vibrations, as indicated by dotted line 93, to output acoustic primary waves in phase opposition to each other. In particular, the two piezoelectric bimorphs 75 and 84 are connected in parallel with each other between the terminal 80 and the ground, thus forming a structure capable of obtaining high transmission power.

While in the above example the piezoelectric bimorphs 75 and 84 are connected by parallel wiring, a serial wiring connection structure may alternatively be formed in which the bimorphs are joined through shim members so that the polarization directions are opposite to each other.

In such a case, if the pair of piezoelectric transducers in the piezoelectric bimorph 75 for example are joined so that the polarization directions are set opposite to each other and in correspondence with directions toward the shim, the polarization directions in the other piezoelectric bimorph 84 for example are set outward. In the case of such a serial configuration, a voltage to be applied is applied between two outer electrodes on opposite sides of the bimorphs. In this case, the electroconductive shim members 78 and 87 are provided only as members for mechanical reinforcement and for mounting to the insulating member 74 on the electroconductive substrate 73.

The above-described configuration enables the piezoelectric bimorphs 75 and 84 to vibrate in phase opposition to each other in a bending vibration manner in response to a drive signal of the same waveform, so that the transmitted acoustic primary waves 83 and 90 are in phase opposition to each other. On the other hand, the piezoelectric transducer thin plate 91 is joined to the electroconductive substrate 73 to form the piezoelectric unimorph supported by the supporting portions 71a.

The terminal 92 for obtaining an output signal is connected to the electrode 60 of the transducer 91. It is easy to adjust the thicknesses of the electroconductive substrate 73 and the piezoelectric transducer 91 and the distance between the supporting portions 71 so that the resonance frequency funi of this piezoelectric unimorph is equal to the frequency of the acoustic secondary wave, i.e., the parametric signal.

Further, in the present embodiment, the unimorph portion is supported by node supports, while the piezoelectric bimorphs 75 and 84 used for transmitting are supported by peripheral supports, as is apparent from FIG. 19. This is for the reason that wider bands of the piezoelectric bimorphs 75 and 84 are preferable because of the need to transmit both the acoustic primary waves of f1 and f2 from the piezoelectric bimorphs 75 and 84, and for the reason that it is preferable to convert only the parametric signal having only the frequency fpara into a voltage at the time of receiving and the node supports by which the resonance Q factor is increased is preferable in doing so.

A modified example of the present embodiment will next be described.

Figure 20:
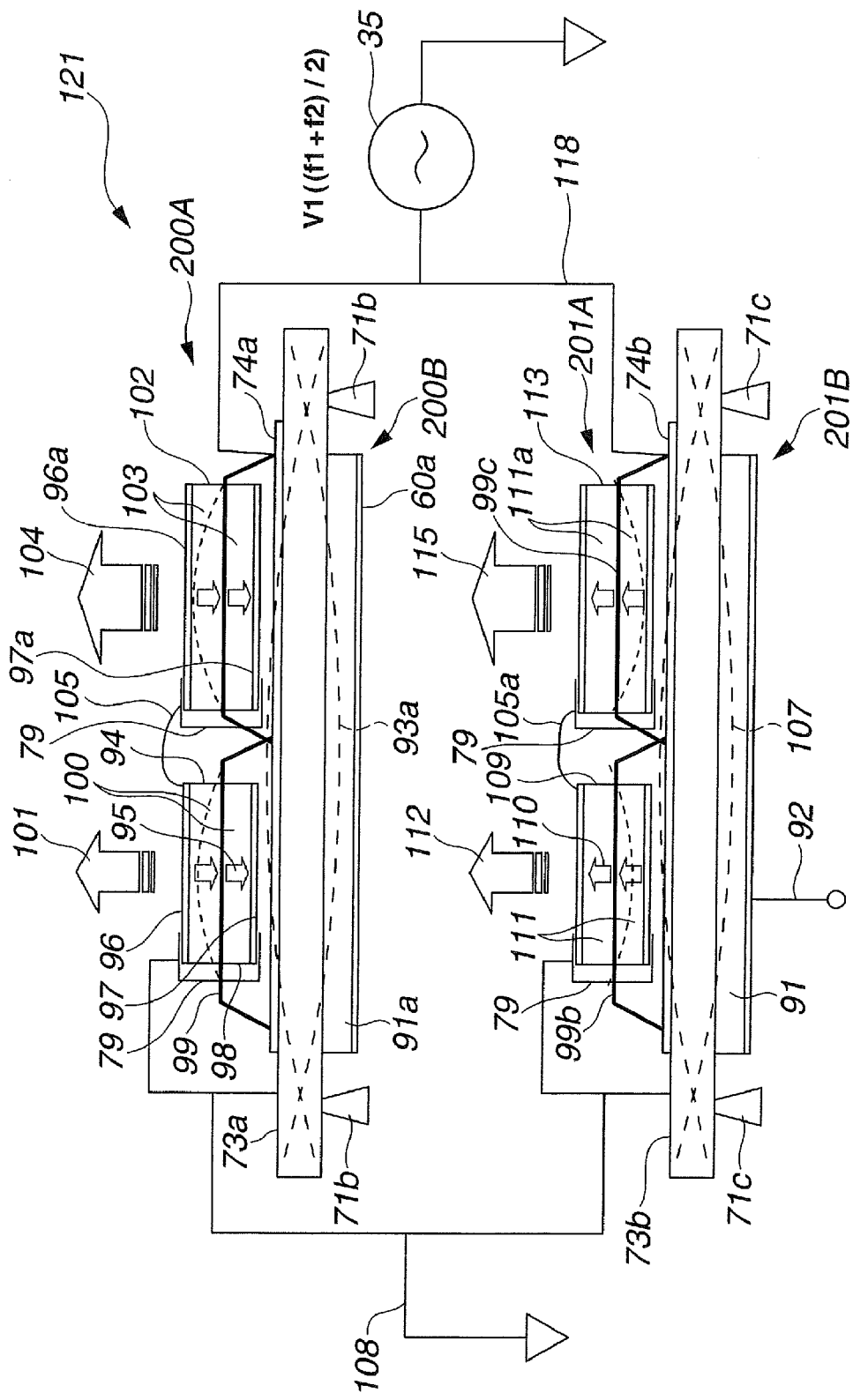
FIG. 20 is a cross-sectional view showing the structure of the parametric acoustic transducer according to the second embodiment of the present invention.
Figure 21:
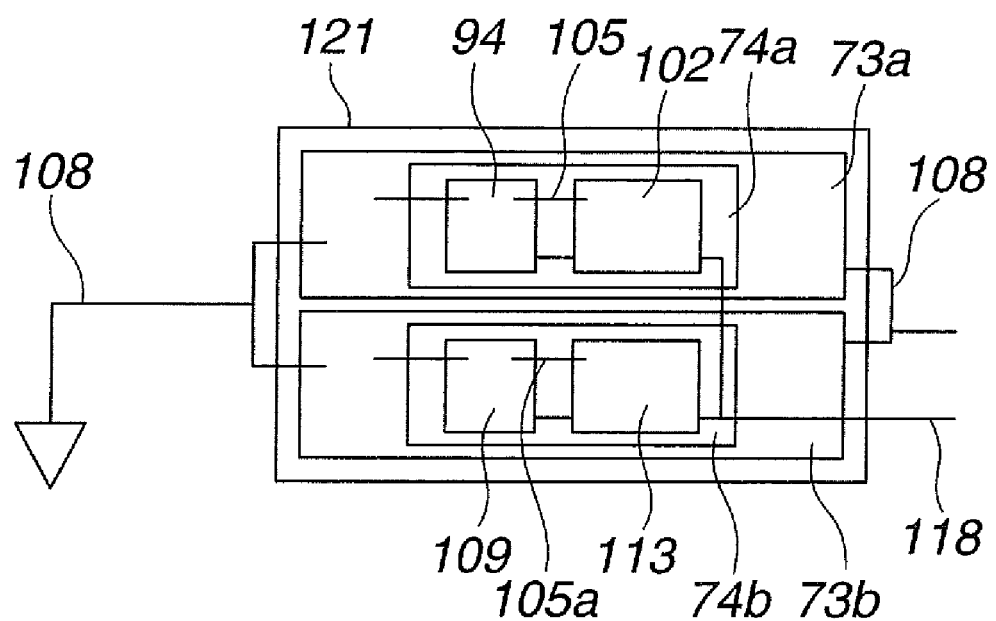
FIG. 21 is a plan view showing the structure of the parametric acoustic transducer according to the second embodiment of the present invention.

FIG. 20 is a cross-sectional view showing the structure of a parametric acoustic transducer according to a modified example of the present embodiment. FIG. 21 is a plan view showing the structure of the parametric acoustic transducer according to the modified example of the present embodiment.

The parametric acoustic transducer in the present modified example uses a piezoelectric bimorph for transmitting acoustic primary waves and a piezoelectric unimorph for receiving an acoustic secondary wave (parametric signal), as does the above-described parametric acoustic transducer in the second embodiment. The parametric acoustic transducer in the present modified example differs in its having a transmitting portion each formed of two transmitting portions (piezoelectric bimorphs 94 and 102, or piezoelectric bimorphs 109 and 113) in two different sizes, i.e., the four piezoelectric bimorphs 94, 102, 109, and 113 in all. The parametric acoustic transducer in the present modified example is advantageous in that the configuration of the drive circuit can be simplified.

As shown in FIG. 20, a transmitting and receiving parametric acoustic transducer 121 is configured by including two transmitting portions 200A and 201A and two receiving portions 200B and 201B.

The transmitting portion 200A is configured by including two piezoelectric bimorphs 94 and 102. The areas of the two piezoelectric bimorphs 94 and 102 are different from each other, as shown in FIG. 21.

Similarly, the transmitting portion 201A is configured by including two piezoelectric bimorphs 109 and 113. The areas of the two piezoelectric bimorphs 109 and 113 are also different from each other, as shown in FIG. 21.

The two piezoelectric bimorphs 94 and 109 are equal in area and thickness to each other, and the two piezoelectric bimorphs 102 and 113 are also equal in areas and thickness to each other.

The transmitting portion 200A is configured by including the piezoelectric bimorphs 94 and 102 each of which generates bending vibration at the time of transmitting an acoustic primary wave.

On one of two surface of an electroconductive substrate 73a (upper surface in FIG. 20), an insulating film of an insulating member 74a is formed. On the other surface of the electroconductive substrate 73a on the opposite side (lower surface in FIG. 20), a piezoelectric-type transducer thin plate 91a is formed by an adhesive or like means.

The piezoelectric transducer thin plate 91a has the electroconductive base substrate 73a as an electrode on one side and has an electrode 60a formed over the entire surface on the other side. The electrode 60a is connected to a terminal 91a. The electroconductive substrate 73a and the piezoelectric transducer thin plate 91a constitute a piezoelectric unimorph. The piezoelectric unimorph is supported by supporting portions 71b at nodes in bending vibration (93a).

On the other hand, a pair of piezoelectric bimorphs 94 and 102 are disposed side by side on the upper surface side of the electroconductive substrate 73a. In the piezoelectric bimorph 94, a pair of piezoelectric transducers 100 are joined together, with an electroconductive shim member 99a interposed therebetween, the pair of piezoelectric transducers 100 having polarization directions corresponding to each other. Also in the piezoelectric bimorph 102, a pair of piezoelectric transducers 103 are joined together, with an electroconductive shim member 99a interposed therebetween, the pair of piezoelectric transducers 103a having polarization directions corresponding to each other. The directions of polarization of the piezoelectric bimorphs 94 and 102 correspond to each other.

Electrodes 96 and 97 are respectively formed on the entire areas of opposite surfaces of the piezoelectric bimorph 94. Also, electrodes 96a and 97a are respectively formed on the entire areas of opposite surfaces of the piezoelectric bimorph 102.

The piezoelectric bimorphs 94 and 102 are respectively supported by the electroconductive shim members 99 and 99a so as to be spaced apart by a predetermined distance from the insulating member 74a. The electrodes 96 and 97 of the piezoelectric bimorph 94 and the electrodes 96a and 97a of the piezoelectric bimorph 102 are connected for electrical conduction through conduction wiring 105.

End portions of the electroconductive shim members 99 and 99a are buckled and one buckled end is fixed on an electrode pad formed on the surface of the insulating member 74a and having electrical conductivity, which electrode pad is not shown in the figure. The electrode pad is connected to the signal source 35.

On the other hand, on the ground side, a common grounding line 108 to which the electrodes 96, 97, 96a, and 97a and the electroconductive substrate 73a are connected is connected to a terminal (not shown in the figure) on the ground side.

The piezoelectric transducers in the piezoelectric bimorphs 94 and 102 are joined together so as to have polarization directions corresponding to each other and set uniformly downward as viewed in FIG. 20.

The two piezoelectric bimorphs 94 and 102 respectively generate bending vibrations as indicated by dotted lines to output acoustic primary waves 101 and 104 at two frequencies f1 and f2 in phase with each other.

The transmitting portion 201A has the same configuration as that of the transmitting portion 200A. That is, the transmitting portion 201A is configured by including the piezoelectric bimorphs 109 and 113 each of which generates bending vibration at the time of transmitting an acoustic primary wave. The configuration of the piezoelectric bimorphs 109 and 113 in the transmitting portion 201A is the same as that of the two piezoelectric bimorphs 94 and 102 in the transmitting portion 200A.

A pair of piezoelectric transducers 111 in the piezoelectric bimorph 109 are joined so as to have polarization directions corresponding to each other. A pair of piezoelectric transducers 111a in the piezoelectric bimorph 113 are also joined so as to have polarization directions corresponding to each other.

The directions of polarization of the piezoelectric bimorphs 109 and 103 correspond to each other, but they are opposite to the directions of polarization of the piezoelectric bimorphs 94 and 102 in the transmitting portion 121A, as shown in FIG. 20.

The piezoelectric bimorphs 109 and 113 are respectively supported by the electroconductive shim members 99b and 99c so as to be spaced apart by a predetermined distance from the insulating member 74b. The two electrodes of the piezoelectric bimorph 102 and the two electrodes of the piezoelectric bimorph 113 are connected for electrical conduction through conduction wiring 105a.

End portions of the electroconductive shim members 99b and 99c are buckled and one buckled end is fixed on an electrode pad formed on the surface of the insulating member 74b and having electrical conductivity, which electrode pad is not shown in the figure. The electrode pad is connected to the signal source 35.

On the other hand, on the ground side, the electrodes at the ends of the bimorphs are wired through conduction wiring 79. The common grounding line 108 to which the eight electrodes in all and the electroconductive substrate 73b are connected is connected to a terminal (not shown in the figure) on the ground side.

The piezoelectric transducers in the piezoelectric bimorphs 109 and 113 are joined together so as to have polarization directions corresponding to each other and set uniformly upward as viewed in FIG. 20.

The two piezoelectric bimorphs 109 and 113 respectively generate bending vibrations as indicated by dotted lines to output acoustic primary waves at two frequencies f1 and f2 in phase with each other.

As described above, the two piezoelectric bimorphs in the transmitting portions differ in size or thickness from each other and are configured so as to have structural sizes with a corresponding difference such that if the resonance frequency of the piezoelectric bimorphs 94 and 109 is f1, the resonance frequency of the piezoelectric bimorphs 102 and 113 is f2. Also, the configuration with respect to the directions of polarization of the piezoelectric elements constituting the piezoelectric bimorphs is such that the polarization directions 95 and 110 are set opposite to each other between the transmitting portions 200A and 201A in order that when in one transmitting portion 200A the piezoelectric bimorph 94 having the resonance frequency f1 for example deforms so that its bending displacement is convex upward, the piezoelectric bimorph 109 having the resonance frequency f1 in the other transmitting portion 201A should deform so that its bending displacement is convex downward. The piezoelectric bimorphs 102 and 113 are also in the same relationship.

The configuration of each of the receiving portions 200B and 201B respectively corresponding to the two transmitting portions 200A and 201A is the same as that of the receiving portion 88B in FIG. 19.

As described above, end portions of the electroconductive shim members 99a to 99d respectively supporting the group of piezoelectric bimorphs are buckled and connected and fixed to the insulating plates formed of the insulating members 74a and 74b formed on the surfaces of the electroconductive substrates 73a and 73b. Further, the electrodes on the opposite sides of the piezoelectric bimorphs 94 and 102 are equipotentially connected by the wiring 105 to the wiring 108 to be grounded. The electrodes on the opposite sides of the piezoelectric bimorphs 109 and 113 are also equipotentially connected by the wiring 105a to the wiring 108 to be grounded. Further, the electroconductive substrates 73a and 73b are also grounded by the wiring 108.

Also, all the electroconductive shim members are equipotentially connected to wiring 118 to be connected to the drive source 35. The drive signal source 35 may have a voltage signal having a single frequency component of (f1+f2)/2. Only one drive source 35 for the two frequency f1 and frequency f2 signals suffices. There is no need for an adder for combining the two signals of frequencies f1 and f2. The acoustic primary waves 101, 104, 112, and 115 generated have two frequency components forming ultrasounds in phase opposition to each other. Further, there is no need for the inverter 9 shown in FIG. 2. Only one amplifier suffices in place of the one pair of amplifiers required. Consequently, the drive control circuit can be made much simpler; the amount of wiring can be largely reduced; and the structure can be easily made more compact as a whole.

The bimorph structure for transmitting and the unimorph structure for receiving may be made by using MEMS manufacturing techniques to achieve similar effects. Needless to say, in such a case, finer bending transducers can be made and, therefore, transmitting/receiving in a MHz band is enabled.

Further, the parametric acoustic transducers according to the present embodiment or the modified example can be used for image forming of a tomographic image or the like, i.e., ultrasound imaging, by performing scanning with a plurality of the parametric acoustic transducers.

Figure 22:
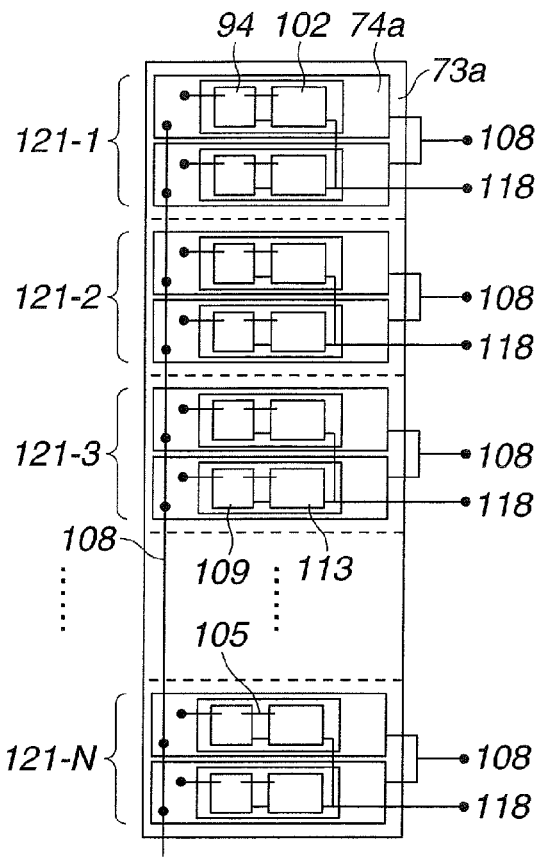
FIG. 22 is a plan view showing an example of a group of acoustic transducers disposed in an array, which is provided by using a plurality of the parametric acoustic transducers according to the second embodiment of the present invention.

FIG. 22 is a plan view showing an example of a group of acoustic transducers disposed in an array, which is provided by using a plurality of the above-described parametric acoustic transducers 121.

The group of acoustic elements shown in FIG. 22 is formed by unidimensionally disposing a plurality of elements 121-1, 121-2, ... 121-N in an array, each element corresponding to the acoustic transducer 121 shown in FIGS. 20 and 21. This configuration is, for example, a transducer configuration for depicting an ultrasound diagnostic image by electronic scanning. Each element has an acoustic primary wave transmitting drive signal input 118, a received signal output terminal (not shown in the figure), wiring 108 forming a common grounding line and a grounding terminal in the wiring. Burst wave pulses having a frequency component of (f1+f2)/2 are successively applied to the plurality of elements between the terminal 118 and a ground (linear electronic scanning), or applied by gradually changing the application timing (sector electronic scanning), and a parametric received signal corresponding to each acoustic primary wave transmission timing is outputted from the wiring terminals 108 to be inputted to a receiving amplifier. Signal processing on the inputted signal and image processing are performed by conventional methods. Therefore these processings will not be described.

As described above, the parametric acoustic transducer according to the second embodiment described above is configured so that both the transmitting portion and the receiving portion generate bending vibrations; the transmitting portion transmits acoustic primary waves; and the receiving portion receives a parametric signal.

According to the present embodiment, an acoustic transducer can be realized which is capable of strongly suppressing acoustic primary waves in the receiving portion, simple in structure and compact.

Third Embodiment

A third embodiment of the present invention will be described.

In the above-described first and second embodiments, a piezoelectric transducer is used in each of the transmitting and receiving portions. The present embodiment differs from the first and second embodiments in its using an electrostatic transducer in each of transmitting and receiving portions.

This electrostatic transducer includes transmitting and receiving of ultrasound by using a cMUT (capacitive Micromachined Ultrasonic Transducer) made by using a MEMS technique. In the present embodiment, a parametric transmitting and receiving device with a cMUT used in an ultrasound endoscope system will be described.

Figure 23:
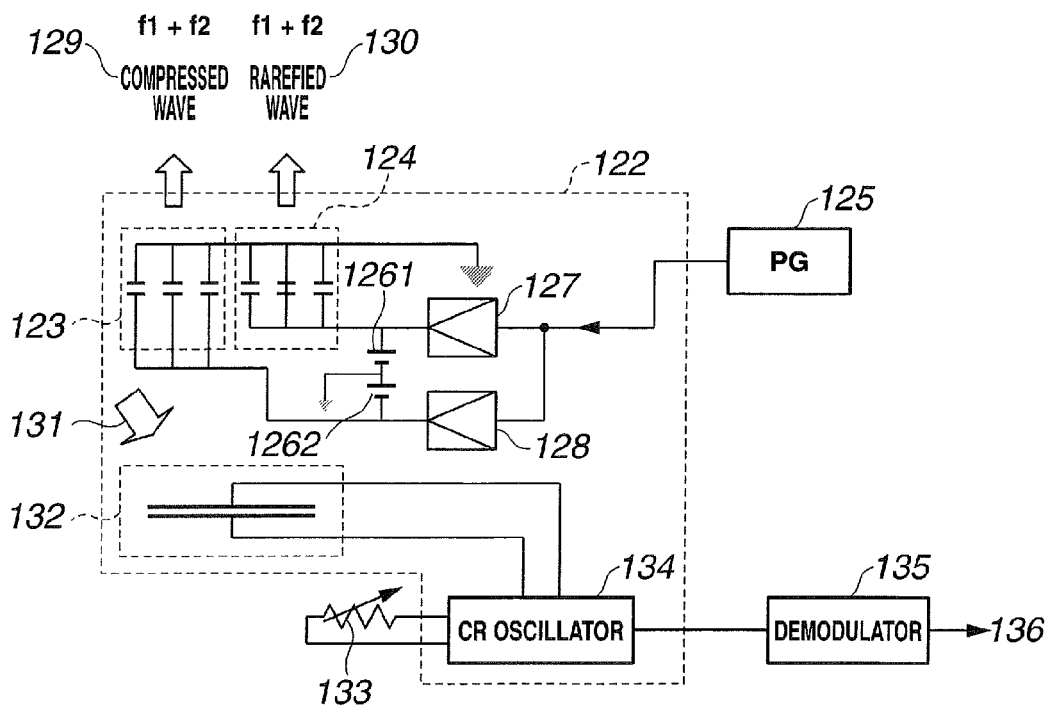
FIG. 23 is a diagram of the configuration of a parametric signal transmitting and receiving system using an electrostatic transducer as a transducer according to a third embodiment of the present invention.
Figure 24:
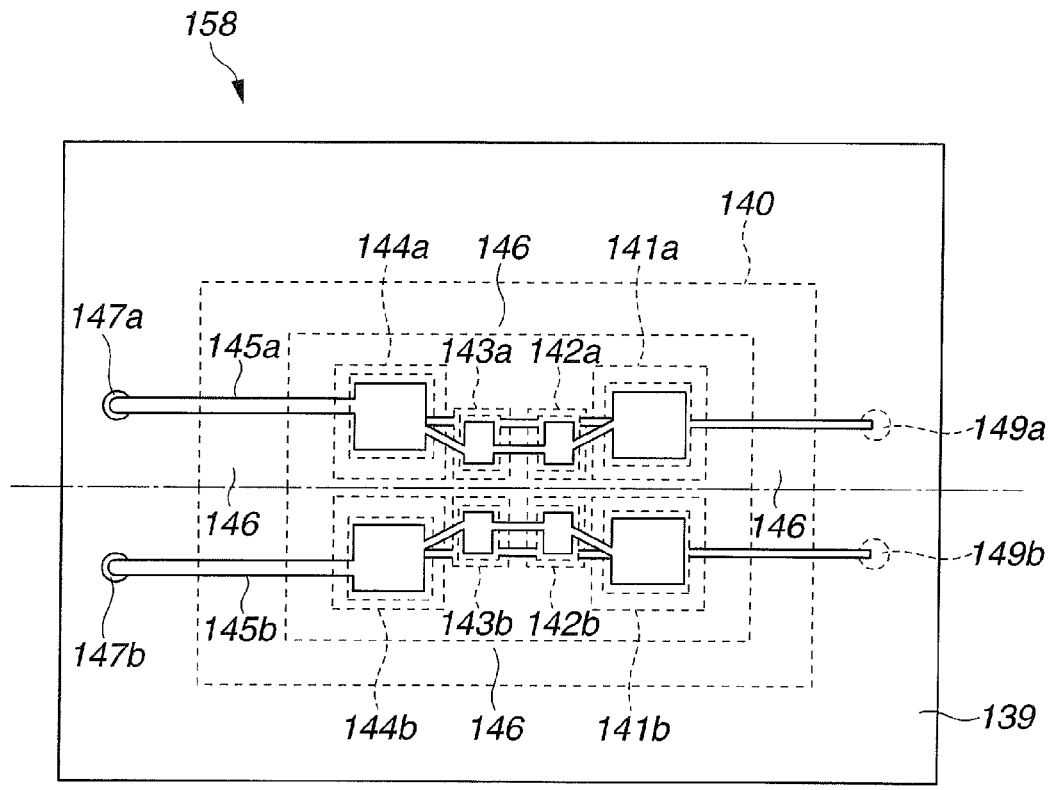
FIG. 24 is a plan view of the electrostatic transducer according to the third embodiment of the present invention.
Figure 25:
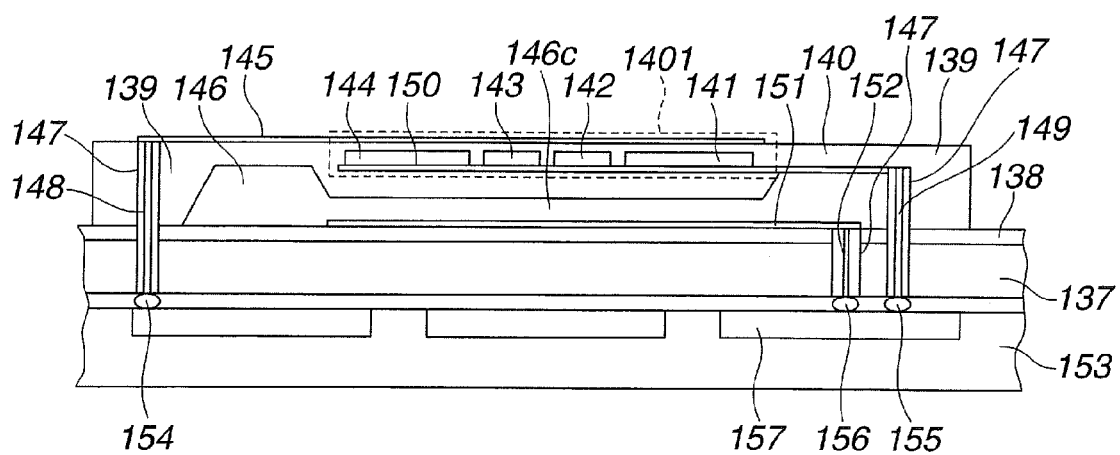
FIG. 25 is a cross-sectional view of the electrostatic transducer according to the third embodiment of the present invention.

FIG. 23 is a diagram of the configuration of a parametric signal transmitting and receiving system using an electrostatic transducer as a transducer according to the present embodiment. FIG. 24 is a plan view of the electrostatic transducer. FIG. 25 is a cross-sectional view of the electrostatic transducer.

Capacitor symbols represent electrostatic-capacity-type transducers C1, C2, and C3. Each transducer is formed on a semiconductor substrate by designing the structural size so that the transducer can generate an ultrasound at its resonance frequency by application of a drive signal having the same frequency as the resonance frequency. The structure of the transducer will be described below with reference to FIGS. 24 and 25.

The structural minimum unit of this electrostatic-capacity-type transducer is called an electrostatic-capacity-type transducer cell. Some electrostatic-capacity-type transducer cells form a group. A unit in which a group of cells are connected in parallel with each other so that one and the same voltage can be applied to all the cells in the group, i.e., a group of transducers surrounded by dot lines 123 or 124 in FIG. 23, is called an electrostatic transducer element.

A parametric signal transmitting and receiving system is configured by including transducer groups C1 and C2 corresponding to elements 123 and 124 as a transmitting portion, a transducer 132 corresponding to an element 132 as a receiving portion, a pulse generator (PG) 125, a bias direct current power supplies 1261 and 1262, power amplifiers 127 and 128, a variable resistor 133, a CR oscillator 134 and a demodulator 135.

One of two electrodes of transducer groups C1 and C2 is connected to a ground. The other terminal of the transducer group C1 is connected to an output of the power amplifier 127. The other terminal of the transducer group C2 is connected to an output of the power amplifier 128.

A point of connection between the two direct current power supplies 1261 and 1262 provided as a DC bias power supply and connected in series is grounded. The other terminal of the direct current power supply 1261 not grounded is connected to the other of the transducer group C1. The other terminal of the direct current power supply 1262 not grounded is connected to the other terminal of the transducer group C2.

An output from the pulse generator 125 is inputted to the power amplifiers 127 and 128. The transducer C3 as the receiving element 132 constitutes a capacitor of the CR oscillator 134. The variable resistor 133 constitutes a resistor of the CR oscillator 134. An output from the CR oscillator 134 is supplied to the demodulator 135, which outputs a detection signal.

Burst pulses having frequency characteristics including both a frequency f1 component and a frequency f2 component for example are outputted from the pulse generator (PG) 125. This signal diverges into one for an output from the power amplifier 128 on which a negative direct current bias voltage is superimposed, and another for an output from the power amplifier 127 on which a positive direct current bias voltage is superimposed. From two regions, drive voltage signals in phase opposition to each other are respectively applied to the electrostatic-capacity-type transducer elements 123 and 124.

The electrostatic-capacity-type transducer elements 123 and 124, indicated by the same capacitor symbols, are respectively constituted by a cell group having a resonance frequency f1 and a cell group having a resonance frequency f2. Accordingly, burst pulses having, for example, such frequency characteristics as to include both a frequency f1 component and a frequency f2 component are applied to the elements 123 and 124 while being DC biased to voltages with opposite polarities equal to or higher than half the voltage of the burst pulses by the direct current power supplies 1261 and 1262. Acoustic primary waves 129 and 130 having frequency f1 and frequency f2 components and in phase opposition to each other are thereby transmitted.

In a propagation medium, e.g., air, water or a living organism, with the propagation of the acoustic primary waves, a parametric signal is generated based on an acoustic nonlinearity of the propagation medium. The parametric signal has a frequency component of |f1−f2|. Therefore the element 132 as an electrostatic ultrasound transducer having such a structure as to resonate with this frequency is disposed and integrally laminated, for example, on the rear surfaces opposite from the acoustic primary wave emergence side of the elements 123 and 124.

There are two methods for receiving the parametric signal. One of them is a method of taking as a received signal changes in electrostatic charge caused with the reception of the parametric signal. In this case, a direct current bias power supply is required at the time of receiving. The other method is a method of associating changes in electrostatic capacity with the reception of the parametric signal with changes in C of the CR oscillator 134, generating a frequency-modulated signal by capturing changes in the oscillation frequency with the changes in C of the CR oscillator, and demodulating the parametric signal by inputting the captured signal to the demodulator 135, as shown in FIG. 23.

In the latter method, the oscillation frequency of the CR oscillator 134 is determined by the product CR of the electrostatic capacity C of the connected capacitor (acoustic secondary wave receiving MEMS electrostatic acoustic transducer) 132 and the direct current resistance R of the resistor 133. The oscillation signal therefrom is frequency modulated according to the received parametric signal. This frequency modulated signal is demodulated to detect the original parametric signal. The method of receiving in this way is particularly convenient in treating a lower-frequency parametric signal.

A technique to detect a received acoustic signal by such frequency modulation/demodulation is disclosed in Japanese Patent Application Laid-Open Publication No. 2008-245715 of the application filed by the applicant of the present invention.

For example, in the case of use for image forming, i.e., imaging of a tomographic image or the like, a demodulated signal 136 undergoes signal processing and image processing so that a tomographic image is displayed on a monitor. For such a purpose, a transmitting/receiving ultrasound transducer 158 (FIG. 24) for such a parametric signal is provided as one element, and a plurality of the elements are unidimensionally or two-dimensionally arrayed to obtain a two-dimensional B mode parametric ultrasound diagnostic image or a three-dimensional B mode parametric ultrasound diagnostic image.

Further, in the present embodiment, conductors in wiring for transmitting and receiving control circuits including an inverter circuit, a transmitting circuit and a receiving circuit and for the electrostatic ultrasound transducers are disposed close to a semiconductor circuit substrate 153 (FIG. 25) on which electrode pads for connection by solder ball bonding means are formed.

With the above-described configuration, there is no need to apply a DC bias voltage at the time of receiving. The above-described configuration is free from the need for impedance conversion, a charge amplifier and a filter, and has merits in improving the degree of integration and in making the transducers compact.

The method of generating acoustic primary waves in phase opposition to each other from the two regions bases on the direct current power supplies 1261 and 1262. These power supplies superimpose a positive bias voltage on the output from the power amplifier 127 on the RF signal from the pulse generator 125, and superimpose a negative bias voltage on the output from the power amplifier 128. When the positive bias voltage is superimposed, the applied voltage is at the maximum in correspondence with a peak of the RF signal. When the negative bias voltage is superimposed, the applied voltage is at the minimum at a peak of the RF signal.

Accordingly, the positive DC voltage and the negative DC voltage are respectively superimposed on the two branch channels to cause the pair of elements (regions) connected to the two branch channels to produce membrane vibration displacements (bending vibrations) in phase opposition to each other, thereby transmitting acoustic primary waves in phase opposition to each other to the ultrasound propagation medium.

In this configuration, even when an ultrasound signal having the same frequency component as that of the acoustic primary waves is received, charges generated by receiving the ultrasound have opposite polarities and, therefore, no receiving voltage is generated. It is necessary to separately configure an electrostatic transducer portion for receiving a parametric signal. The positive and negative DC bias voltages may be disposed in a stage before the power amplifiers 127 and 128.

Methods conceivable as a method of generating two acoustic waves in phase opposition to each other from the two regions, as well as the method using a pair of direct current power supplies as described above, include a method of forming an inverter in one of the two branch channels, a method of replacing the power amplifiers with a combination of inverting-type and noninverting-type power amplifiers, and a method of forming two branch lines after the stage of amplification by one power amplifier and connecting a pair of direct current power supplies so that positive and negative direct current biases are respectively superimposed on the two branch lines. One of these methods considered most suitable is used.

The structure of the acoustic transducer including each element will next be described.

FIGS. 24 and 25 show an example of forming by a MEMS technique an acoustic transducer for transmitting and receiving a parametric signal. In FIG. 24, symbol "a" attached to reference numerals denotes a structural member in a region for transmitting a normal-phase acoustic primary wave, and symbol "b" denotes a structural member in a region for transmitting an opposite-phase acoustic primary wave.

The acoustic transducer has as a receiving portion, a structure in which a first electrostatic capacity cell of a large diameter on a silicon high-resistance semiconductor substrate 137 having its surface oxidized, and in which a plurality of groups of second electrostatic capacity cells of a small diameter (in broken line area 1401) are formed as a transmitting portion in a membrane 140 of the first electrostatic capacity cell.

As shown in FIGS. 24 and 25, an integrated circuit 157 including various circuits is formed on the semiconductor substrate 153. Connecting pieces of solder 154, 155, 156 on the integrated circuit 157 are connected to conductors 148, 149, and 152 for which insulation is secured by forming an insulating layer 147 in via holes (hole portions) formed in the silicon substrate 137. An insulating layer 138 is provided on the silicon substrate 137.

A lower electrode 151 of a cMUT for acoustic secondary wave receiving is provided on the insulating layer 138. The lower electrode 151 is connected to the integrated circuit 157 through via wiring 152 and connecting piece of solder 156.

The membrane 140 having a peripheral supporting portion 139 and having a thicker central portion 146c and a thinner peripheral portion 146 such that a cavity is formed therein is provided on the insulating layer 138.

In the central portion 146c of the membrane 140, the transducer groups C1 and C2 constituting the transmitting portion are formed. The transducer group C1 includes cavities (for f1) 141 and 144 of the acoustic primary wave transmitting cMUT. The transducer group C2 includes cavities (for f2) 142 and 143 of the acoustic primary wave transmitting cMUT. Electrodes are respectively formed on the upper and lower sides of the cavities. The electrode 150 on the lower side is connected to electrode wiring 145 for connection to the power amplifiers 127 and 128 such as shown in FIG. 23. The electrode on the upper side constitutes a cMUT element upper electrode 145 for the acoustic primary waves and is connected to wiring on the ground side.

An insulating layer and a protective film, not shown in the figure, may be formed over the upper electrode 145 to improve the mechanical strength.

The wiring on the ground side is connected to the connecting piece of solder 154 through via wiring 148. Electrode wiring 150 is connected to the connecting piece of solder 155 through via wiring 149. The lower electrode 151 for acoustic secondary wave receiving is connected to the connecting piece of solder 156 through the via wiring 152 passing through the through hole 147.

The upper electrode 150 for the acoustic secondary wave also serving as a lower electrode for acoustic primary waves and the lower electrode 151 for the acoustic secondary wave constitute a receiving portion. To receive a reflected wave of the acoustic secondary wave generated with propagation of the acoustic primary waves, the receiving portion is disposed so that the region for receiving the reflected wave is superimposed on the transmitting portion as viewed along the direction of transmission of the acoustic primary waves.

According to the present embodiment, as described above, a pair of units each having a membrane in which a plurality of cells (a plurality of transducers) of small two sizes for transmitting acoustic primary waves are gathered, and a cell (transducer) formed on the semiconductor substrate side of the membrane and having a size larger than the plurality of cells having the two sizes, are disposed adjacent to each other, and signals in phase opposition to each other are applied to the units.

Thus, according to the present embodiment, an acoustic transducer can be realized which is capable of strongly suppressing acoustic primary waves in the receiving portion, simple in structure and compact.

A modified example of the present embodiment will next be described.

Figure 26:
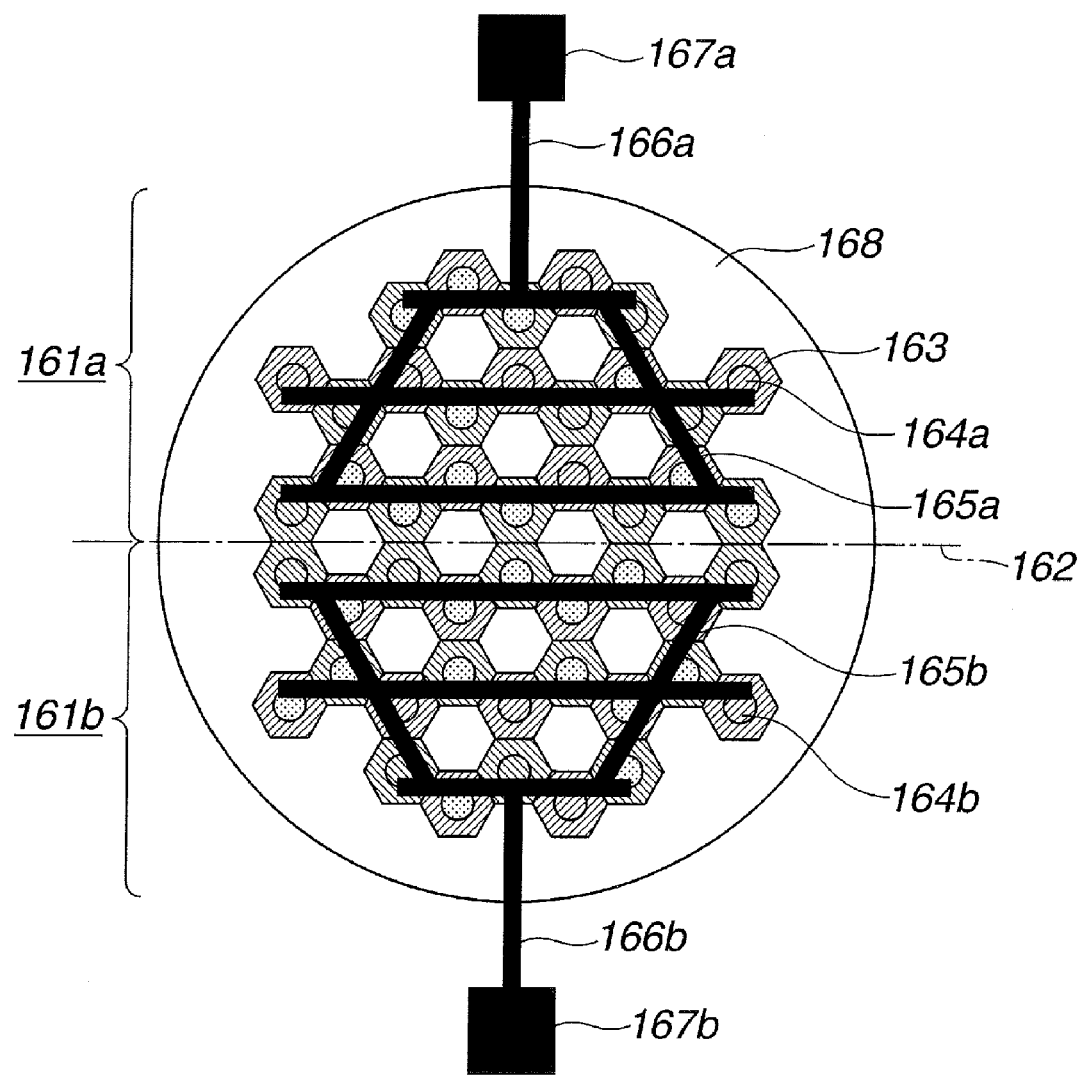
FIG. 26 is a plan view showing the structure of a parametric acoustic transducer according to a modified example of the third embodiment of the present invention.

FIG. 26 is a plan view showing the structure of a parametric acoustic transducer according to a modified example of the present embodiment. This modified example relates, for example, to a structure for obtaining an image such as an ultrasound diagnostic image.

As shown in FIG. 26, the parametric acoustic transducer in the present modified example is a single-plate transducer having a circular opening. To obtain an ultrasound diagnostic image, ultrasound is transmitted and received while moving an ultrasound beam for scanning by mechanical rotation. In this way, an ultrasound diagnostic image with a larger penetration depth can be obtained.

On a circular semiconductor substrate 168, a plurality of electrostatic-capacity-type ultrasound transducer cells 163 each having a hexagonal shape are integrally disposed symmetrically with respect to a boundary line 162 while being divided into a region 161a and a region 161b.

The plurality of cells in each region have connections established between upper electrodes 164a or 164b by wiring 165a or 165b. In the region 161a, pieces of wiring 165a and 166a and an electrode pad 167a are disposed while being connected for conduction. Also, in the region 161b, pieces of wiring 165a and 166b and an electrode pad 167b are disposed while being connected for conduction.

In each region 161a or 161b, the plurality of cells 163 are disposed so that each adjacent pair of cells are cells having resonance frequencies different from each other. By disposing the cells in this way, the facility with which a parametric signal is generated from acoustic primary waves is improved.

Receiving of a parametric echo signal is performed through an electrostatic-capacity-type ultrasound transducer formed by a membrane of a large size containing both the regions 161a and 161b. The structure of the transducer is the same as that shown in FIG. 25. While each cell 163 is hexagonal in this example, the cells may alternatively have any other shape, e.g., the shape of a circle or the shape of any other polygon.

Ground-side electrodes (not shown) of the hexagonal cells 163 of the electrostatic-capacity-type ultrasound transducer are formed so that all the cells on the substrate 168 can be driven in correspondence with each of the regions 161a and 161b where the cells are connected by common wiring to be grounded. The grounding structure is the same as that in which, as shown in FIG. 25, the upper electrode is connected via the through wiring provided in the through hole 147 to a grounding electrode pad on the semiconductor substrate 153 joined to the back surface of the substrate 137 by bonding or like means.

In a case where various control circuits are monolithically provided in a layer below the MEMS transducer in the silicon substrate 137, the upper electrode may be directly connected to the ground line of the control circuits.

In a case where all the cells 163 have such a cell structure that the cells have the same structural size and the same resonance characteristic, each of voltage signals applied to the terminals 167a and 167b has a signal combining the frequency f1 and the frequency f2, and the voltage signals are in phase opposition to each other.

In a case where each cell is designed so that two membrane sizes are set such that the cell has resonance frequencies f1 and f2, wide-band drive signals each of which has a spectrum including the frequency f1 and the frequency f2 and which are in phase opposition to each other are inputted through the respective electrode pads.

According to the present embodiment and the modified examples, the electrostatic MEMS transducer is formed on the surface of a silicon semiconductor substrate, has control circuits, e.g., a signal generator, an inverter circuit and a receiving circuit monolithically made therein, as shown in the section of the structure shown in FIG. 25, and can be structured so as to be compact as a whole. Therefore, the transducer can be easily incorporated in various ultrasound diagnosis apparatuses, such as an ultrasound endoscope, an IVUS (Intra Vascular Ultrasound) and a capsule-type ultrasound endoscope, which are used in a narrow space, and which need to be reduced in size and diameter.

An example of electronic appliances to which the transmitting and receiving parametric acoustic transducers according to the embodiments described above can be applied will be described.

Figure 27:
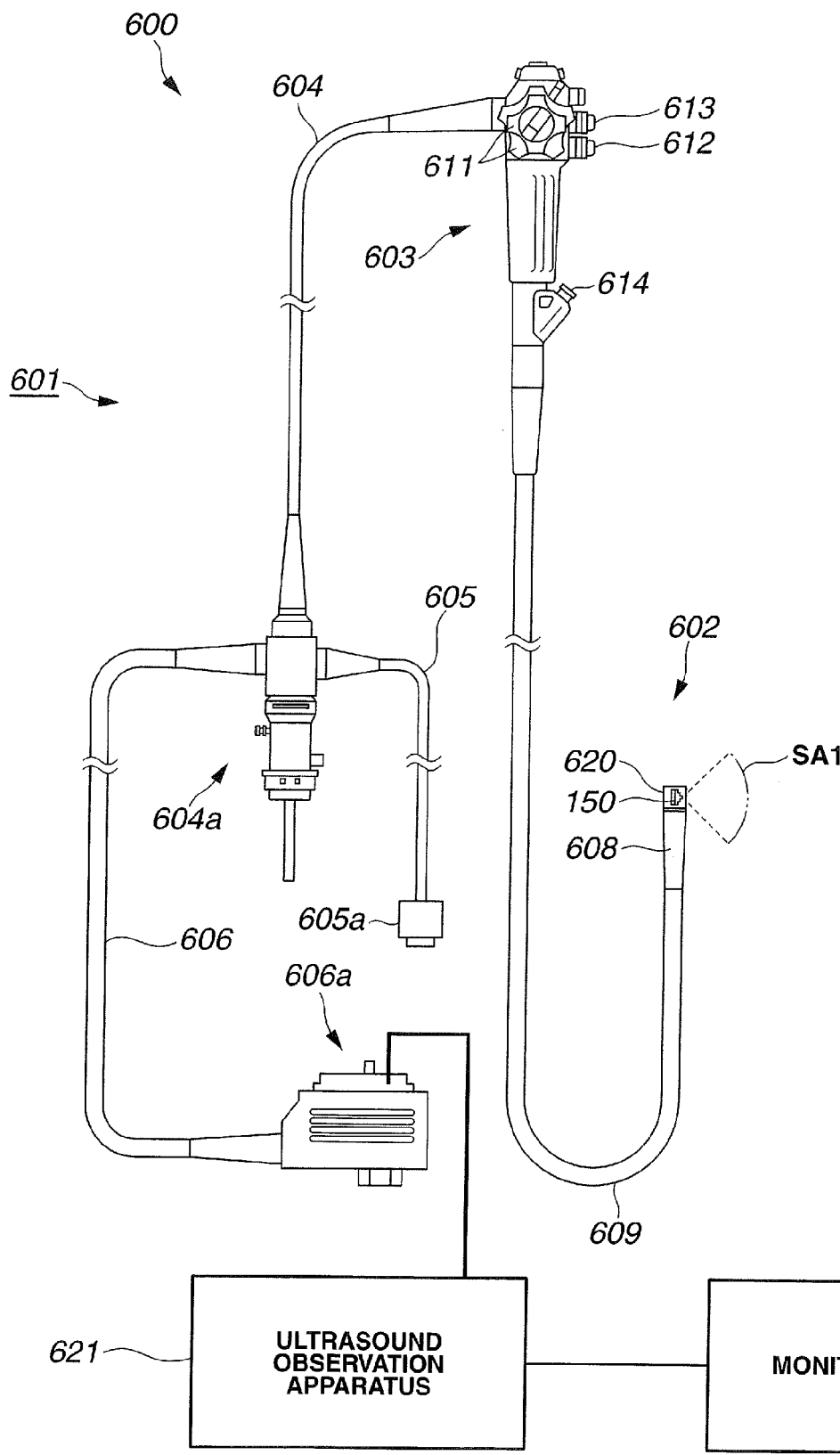
FIG. 27 is a diagram showing the configuration of an ultrasound endoscope system having an ultrasound endoscope using as an ultrasound transducer one of the transmitting and receiving parametric acoustic transducers described in the description of the embodiments of the present invention.

FIG. 27 is a diagram showing the configuration of an ultrasound endoscope system having an ultrasound endoscope using as an ultrasound transducer one of the transmitting and receiving parametric acoustic transducers described in the above description of the embodiments.

As shown in FIG. 27, an ultrasound endoscope 600 is constituted mainly by an elongated insertion portion 602 to be introduced into the body of a subject, an operation portion 603 positioned at the proximal end of the insertion portion 602, and a universal cord 604 extending from a side portion of the operation portion 603.

An endoscope connector 604a to be connected to a light source not shown in the figure is provided in a proximal end portion of the universal cord 604. From this endoscope connector 604a, an electric cable 605 detachably connected to a camera control unit not shown in the figure through an electric connector 605a and an ultrasound cable 606 detachably connected to an ultrasound observation apparatus 621 through an ultrasound connector 606a are extended.

The insertion portion 602 is configured by successively disposing from the distal end side a distal end rigid portion 620 formed of a hard member, a bending portion 608 freely bendable positioned at the rear end of the distal end rigid portion 620, and a flexible tube portion 609 positioned at the rear end of the bending portion 608, extending to a distal end portion of the operation portion 603, having a small diameter, elongated and having flexibility. An ultrasound transducer 150 is provided on the distal end side of the distal end rigid portion 620. This ultrasound transducer 150 includes a plurality of the transmitting and receiving parametric acoustic transducers described above.

The operation portion 603 is provided with an angle knob 611 for controlling bending of the bending portion 608 in a desired direction, an air/water feed button 612 for performing air feed or water feed operation, a suction button 613 for performing a suction operation, and a treatment instrument insertion port 614 as an inlet for a treatment instrument to be introduced into a tubular body cavity or a body cavity.

Through the ultrasound transducer 150 provided on the distal end of the distal end rigid portion 620, the ultrasound endoscope 600 can obtain an ultrasound image in a scanning area SA1.

Also, the distal end rigid portion 120 is provided with an illumination lens constituting an illumination optic portion for applying illumination light to a portion to be observed, an observation optic portion for capturing an optical image of a portion to be observed, a suction/forceps port which is an opening through which a cut portion is suctioned or a treatment instrument is protruded out, and an air/water feed port through which air feed or water feed is performed.

The ultrasound transducer 150 shown in FIG. 27 is applicable not only to the ultrasonic endoscope 600, which is an image generation apparatus for generating an ultrasound image, but also to an ultrasound diagnosis system which is a well-known electronic appliance. More specifically, the ultrasound transducer may be applied to an external ultrasound probe for observing an inner body portion of a subject from the outside of the body of the subject.

Figure 28:
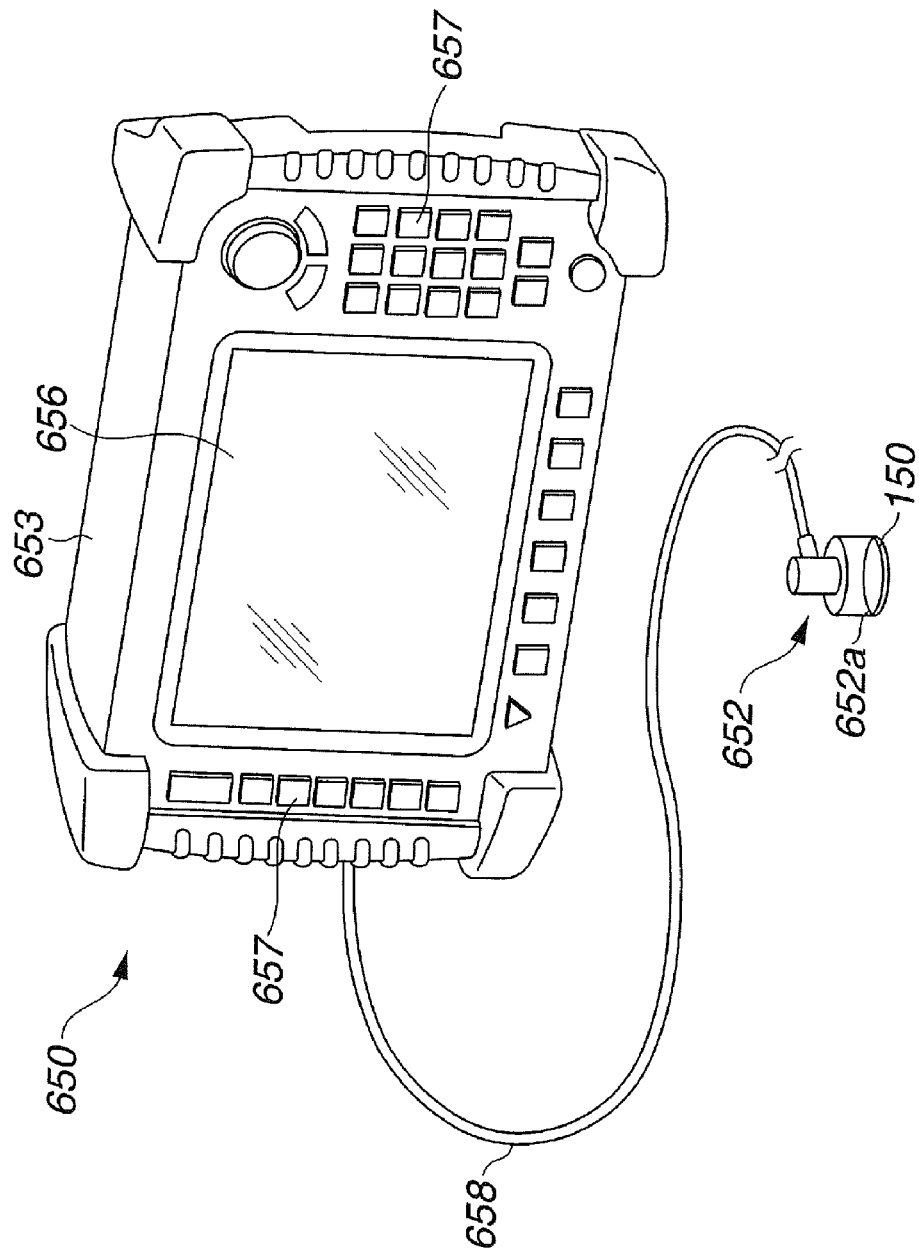
FIG. 28 illustrates an application of one of the transmitting and receiving parametric acoustic transducers described in the description of the embodiments of the present invention to an ultrasound flaw detector as an example of a nondestructive inspection apparatus.

FIG. 28 illustrates an application of one of the transmitting and receiving parametric acoustic transducers described above in the description of the embodiments to an ultrasound flaw detector as an example of a nondestructive inspection apparatus. FIG. 28 is a diagram schematically showing the configuration of the ultrasound flaw detector.

The ultrasound flaw detector 650 is an image generation apparatus which generates an ultrasound image, and which has a probe 652 through which ultrasound is transmitted or received, and an apparatus main body portion 653 in box form for controlling the probe 652.

A display device 656 for displaying an image for flaw detection is provided in a front surface of the apparatus main body portion at a center thereof. Switches 657 having various roles are provided in the vicinity of the display device 656.

The probe 652 is connected to the apparatus main body portion 653 by a composite coaxial cable 658. In the probe 652, one ultrasound transducer 150 or a plurality of ultrasound transducers 150 are provided in a contact surface portion 652a by which the probe 652 contacts a subject.

By emitting ultrasound in a state of having its contact surface portion 652a of the probe 652 maintained in contact with a subject, the ultrasound flaw detector 650 can detect a flaw in the subject through changes in reflection of the ultrasound without destroying the subject.

The ultrasound transducer 150 described in the description of any of the above-described embodiments is applicable not only to the above-described ultrasound flaw detector but also to a nondestructive inspection apparatus which is a well known electronic appliance. For example, the ultrasound transducer 150 may be applied to a thickness measuring apparatus for measuring the thickness of a subject by transmitting and receiving ultrasound.

The present invention is not limited to the above-described embodiments. Various changes can be made in the described embodiments as desired as long as the changes do not depart from the gist or spirit of the invention that can be read from the appended claims and the entire specification. Ultrasound transducers and electronic appliances including such changes also come within the technical scope of the present invention.

According to the present invention, as described above, an acoustic transducer capable of strongly suppressing acoustic primary waves in the receiving portion, simple in structure and compact can be realized by utilizing the essential characteristics of a parametric signal, i.e., a small attenuation, capability of propagating an acoustic wave signal through a large distance, and a directionality much higher than that of a fundamental wave of the same frequency.

The present invention is not limited to the above-described embodiments. Various changes, modifications and the like can be made in the embodiments without departing from the gist of the invention.

What is claimed is:

1. An acoustic transducer used for observing a subject, comprising:
   a first transducer which transmits, to a subject, a first acoustic primary wave including a first ultrasound and a second acoustic primary wave including a second ultrasound different from the first ultrasound in frequency, in a superimposed manner; and
   a second transducer which is arranged in a region for receiving a reflected wave which hit and reflected from the subject, the reflected wave being an acoustic secondary wave generated at a part where the first and second acoustic primary waves are superimposed to each other, from among acoustic secondary waves as nonlinear acoustic waves whose frequency components have changed along with propagation of the first and second acoustic primary waves, the second transducer resonating with a frequency component of the acoustic secondary wave for receiving the reflected wave, wherein the first transducer has a first region for transmitting the first acoustic primary wave and a second region for transmitting the second acoustic primary wave, transmissions from the first and second regions being made in phase opposition to each other.

2. The acoustic transducer according to claim 1, wherein the acoustic secondary wave has a frequency component corresponding to the difference between the frequencies of the first ultrasound and the second ultrasound or the sum of the frequencies of the first ultrasound and the second ultrasound.

3. The acoustic transducer according to claim 1, wherein the first transducer has a first diaphragm corresponding to the first ultrasound and a second diaphragm corresponding to the second ultrasound, a polarization direction of the first diaphragm and a polarization direction of the second diaphragm are opposite to each other, a first common electrode is provided on one surface of the first diaphragm and one surface of the second diaphragm, and a second common electrode is provided on another surface of the first diaphragm and another surface of the second diaphragm.

4. The acoustic transducer according to claim 3, wherein the two diaphragms respectively include diaphragms each of which produces thickness longitudinal vibration along the polarization direction, the acoustic primary wave being transmitted by the thickness longitudinal vibration.

5. The acoustic transducer according to claim 1, wherein a frequency-reducing member for reducing a frequency of the first ultrasound and generating the second ultrasound is provided on a part of a front surface or on a part of a rear surface of the first transducer.

6. The acoustic transducer according to claim 1, wherein the second transducer includes a diaphragm which receives the acoustic secondary wave and produces bending vibration along the polarization direction.

7. An image generation apparatus which generates an image by disposing a plurality of the acoustic transducers according to claim 1 in an array or in a planar form, and by scanning an object with the acoustic primary wave.

8. The image generation apparatus according to claim 7, wherein the image is an ultrasound image.

9. An acoustic transducer used for observing a subject, comprising:

a first transducer which transmits, to a subject, a first acoustic primary wave including a first ultrasound and a second acoustic primary wave including a second ultrasound different from the first ultrasound in frequency, in a superimposed manner; and a second transducer which is arranged in a region for receiving a reflected wave which hit and reflected from the subject, the reflected wave being an acoustic secondary wave generated at a part where the first and second acoustic primary waves are superimposed to each other, from among acoustic secondary waves as nonlinear acoustic waves whose frequency components have changed along with propagation of the first and second acoustic primary waves, the second transducer resonating with a frequency component of the acoustic secondary wave for receiving the reflected wave, wherein the first transducer is arranged in a superimposed manner so as to be at a front surface or a rear surface of the second transducer as seen along the direction of transmission of the first acoustic primary wave and the second acoustic primary wave, and further the first transducer and the second transducer are formed by being attached to each other.

10. An acoustic transducer used for observing a subject, comprising:

a first transducer which transmits, to a subject, a first acoustic primary wave including a first ultrasound and a second acoustic primary wave including a second ultrasound different from the first ultrasound in frequency, in a superimposed manner; and a second transducer which is arranged in a region for receiving a reflected wave which hit and reflected from the subject, the reflected wave being an acoustic secondary wave generated at a part where the first and second acoustic primary waves are superimposed to each other, from among acoustic secondary waves as nonlinear acoustic waves whose frequency components have changed along with propagation of the first and second acoustic primary waves, the second transducer resonating with a frequency component of the acoustic secondary wave for receiving the reflected wave, wherein the first transducer has a first diaphragm corresponding to the first ultrasound and a second diaphragm corresponding to the second ultrasound, a direction of polarization of the first diaphragm and a direction of polarization of the second diaphragm are same to each other, a common electrode is provided on one surface of the first diaphragm and on one surface of the second diaphragm, and a first electrode and a second electrode are respectively provided on another surface of the first diaphragm and another surface of the second diaphragm.

11. An acoustic transducer used for observing a subject, comprising:

a first transducer which transmits, to a subject, a first acoustic primary wave including a first ultrasound and a second acoustic primary wave including a second ultrasound different from the first ultrasound in frequency, in a superimposed manner; and a second transducer which is arranged in a region for receiving a reflected wave which hit and reflected from the subject, the reflected wave being an acoustic secondary wave generated at a part where the first and second acoustic primary waves are superimposed to each other, from among acoustic secondary waves as nonlinear acoustic waves whose frequency components have changed along with propagation of the first and second acoustic primary waves, the second transducer resonating with a frequency component of the acoustic secondary wave for receiving the reflected wave, wherein the first transducer is arranged in a superimposed manner so as to be on a front surface or a rear surface of the second transducer as seen along the direction of transmission of the first acoustic primary wave and the second acoustic primary wave, and further the first transducer and the second transducer are disposed by being spaced apart from each other.

12. The acoustic transducer according to claim 11, wherein the first transducer includes a first diaphragm corresponding to the first ultrasound and a second diaphragm corresponding to the second ultrasound, and the first diaphragm and the second diaphragm generate ultrasound by bending action.

13. The acoustic transducer according to claim 12, wherein the two diaphragms are each piezoelectric bimorphs.

14. The acoustic transducer according to claim 11, wherein the second transducer includes a diaphragm which receives the acoustic secondary wave and produces bending vibration.

15. The acoustic transducer according to claim 14, wherein the second transducer is a piezoelectric unimorph.

16. The acoustic transducer according to claim 11, wherein the first transducer includes a first diaphragm corresponding to the first ultrasound and a second diaphragm corresponding to the second ultrasound, the first diaphragm and the second diaphragm generate ultrasound by bending action and the first diaphragm and the second diaphragm generate ultrasounds with frequencies different to each other by having dimensions or thicknesses different to each other.

17. The acoustic transducer according to claim 16, wherein the second transducer includes a diaphragm which receives the acoustic secondary wave and produces bending vibration.

18. An acoustic transducer used for observing a subject, comprising:

a first transducer which transmits, to a subject, a first acoustic primary wave including a first ultrasound and a second acoustic primary wave including a second ultrasound different from the first ultrasound in frequency, in a superimposed manner; and a second transducer which is arranged in a region for receiving a reflected wave which hit and reflected from the subject, the reflected wave being an acoustic secondary wave generated at a part where the first and second acoustic primary waves are superimposed to each other, from among acoustic secondary waves as nonlinear acoustic waves whose frequency components have changed along with propagation of the first and second acoustic primary waves, the second transducer resonating with a frequency component of the acoustic secondary wave for receiving the reflected wave, wherein each of the first transducer and the second transducer is an electrostatic transducer.

19. The acoustic transducer according to claim 18, wherein the electrostatic transducer is formed by MEMS on a substrate.

20. The acoustic transducer according to claim 18, wherein the first transducer is formed in a membrane of the second transducer.

21. The acoustic transducer according to claim 18, wherein wiring is arranged so that polarities of direct current voltages respectively applied to the first transducer and the second transducer are opposite to each other.

22. The acoustic transducer according to claim 18, wherein transducer cells constituting the first transducer and the second transducer include a cell having a resonance frequency f1 and a cell having a resonance frequency f2, the cell having the resonance frequency f1 and the cell having the resonance frequency f2 being integrally disposed adjacent to each other.

23. The acoustic transducer according to claim 22, wherein shapes of the cells constituting the first transducer and the second transducer are hexagonal.

24. The acoustic transducer according to claim 18, wherein an opening of the acoustic transducer constituted by the first transducer and the second transducer is circular and has an axis of rotation.

* * * * *